(12) United States Patent  
Leach et al.

(10) Patent No.: US 7,992,725 B2
(45) Date of Patent: *Aug. 9, 2011

(54) BUOY SUSPENSION FRACTIONATION SYSTEM

(75) Inventors: Michael D. Leach, Warsaw, IN (US); Randel Dorian, San Diego, CA (US); Jacy C. Hoeppner, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 521 days.

This patent is subject to a terminal disclaimer.

(21) Appl. No.: 12/101,586

(22) Filed: Apr. 11, 2008

(65) Prior Publication Data

US 2009/0014391 A1   Jan. 15, 2009

Related U.S. Application Data

(60) Provisional application No. 60/911,407, filed on Apr. 12, 2007.

(51) Int. Cl.
*B01D 21/26* (2006.01)
*B01D 45/12* (2006.01)
*B04B 5/02* (2006.01)
*B04B 7/00* (2006.01)

(52) U.S. Cl. .......... 210/518; 210/789; 210/512.1; 494/16; 494/38; 422/918

(58) Field of Classification Search .......... None
See application file for complete search history.

(56) References Cited

U.S. PATENT DOCUMENTS

| 280,820 | A | 7/1883 | Hickson et al. |
| 593,333 | A | 11/1897 | Park |
| 1,468,313 | A | 9/1923 | Lux |
| 1,593,814 | A | 7/1926 | Vogel |
| 2,553,004 | A | 5/1951 | Rabatine |
| 2,722,257 | A | 11/1955 | Lockhart |
| 3,013,557 | A | 12/1961 | Pallotta |
| 3,159,159 | A | 12/1964 | Cohen |
| 3,409,165 | A | 11/1968 | Creith |
| 3,441,143 | A | 4/1969 | Kudlaty |
| 3,453,364 | A | 7/1969 | Flodin et al. |
| 3,469,369 | A | 9/1969 | Helmke |

(Continued)

FOREIGN PATENT DOCUMENTS

AU   696278   1/1999

(Continued)

OTHER PUBLICATIONS

Jayadev, Suprya. "Trypsinization of Adherent Cells." Aug. 8, 1991. Web. Apr. 14, 2010 http://www.duke.edu/web/ceramide/protocols/0005.html.

(Continued)

*Primary Examiner* — Krishnan S Menon
(74) *Attorney, Agent, or Firm* — Harness, Dickey

(57) ABSTRACT

A separator that uses centrifugation to fractionate a suspension such as blood comprises a separation container and a buoy. The buoy is carried in the separation container and has a tuned density that is configured to reach an equilibrium position in a suspension. The guide surface is carried on the buoy upper surface and is inclined to an accumulation position near a buoy perimeter. The buoy suspension fractionation system can be used in a method of isolating a fraction from a suspension, and in a method for re-suspending particulates for withdrawal.

53 Claims, 14 Drawing Sheets

U.S. PATENT DOCUMENTS

| | | |
|---|---|---|
| 3,508,653 A | 4/1970 | Coleman |
| 3,545,671 A | 12/1970 | Ross |
| 3,596,652 A | 8/1971 | Winkelman |
| 3,706,305 A | 12/1972 | Berger et al. |
| 3,706,306 A | 12/1972 | Berger et al. |
| 3,723,244 A | 3/1973 | Breillatt, Jr. |
| 3,779,383 A | 12/1973 | Ayres |
| 3,785,549 A | 1/1974 | Latham, Jr. |
| 3,814,248 A | 6/1974 | Lawhead |
| 3,850,369 A | 11/1974 | Bull et al. |
| 3,879,295 A | 4/1975 | Glover et al. |
| 3,894,952 A | 7/1975 | Ayres |
| 3,896,733 A | 7/1975 | Rosenberg |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,937,211 A | 2/1976 | Merten |
| 3,941,699 A | 3/1976 | Ayres |
| 3,951,801 A | 4/1976 | Ayres |
| 3,957,654 A | 5/1976 | Ayres |
| 3,965,889 A | 6/1976 | Sachs |
| 3,972,812 A | 8/1976 | Gresl, Jr. |
| 3,982,691 A | 9/1976 | Schlutz |
| 4,001,122 A | 1/1977 | Griffin |
| 4,020,831 A | 5/1977 | Adler |
| 4,046,699 A | 9/1977 | Zine, Jr. |
| 4,055,501 A | 10/1977 | Cornell |
| 4,059,108 A | 11/1977 | Latham, Jr. |
| 4,077,396 A | 3/1978 | Wardlaw et al. |
| 4,088,582 A | 5/1978 | Murty et al. |
| 4,146,172 A | 3/1979 | Cullis et al. |
| 4,152,270 A | 5/1979 | Cornell |
| 4,154,690 A | 5/1979 | Ballies et al. |
| 4,159,896 A | 7/1979 | Levine et al. |
| 4,187,979 A | 2/1980 | Cullis et al. |
| 4,204,537 A | 5/1980 | Latham, Jr. |
| 4,225,580 A | 9/1980 | Rothman et al. |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. et al. |
| 4,322,298 A | 3/1982 | Persidsky |
| 4,362,567 A | 12/1982 | Schwarz et al. |
| 4,364,832 A | 12/1982 | Ballies et al. |
| 4,377,572 A | 3/1983 | Schwarz et al. |
| 4,379,849 A | 4/1983 | Heimreid et al. |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi et al. |
| 4,427,650 A | 1/1984 | Stroetmann et al. |
| 4,427,651 A | 1/1984 | Stroetmann et al. |
| 4,442,655 A | 4/1984 | Stroetmann et al.. |
| 4,443,345 A | 4/1984 | Wells |
| 4,446,021 A | 5/1984 | Aufderhaar et al. |
| 4,453,927 A | 6/1984 | Sinko |
| 4,453,939 A | 6/1984 | Zimmerman et al. |
| 4,464,167 A | 8/1984 | Schoendorfer et al. |
| 4,511,662 A | 4/1985 | Baran et al. |
| 4,537,767 A | 8/1985 | Rothman et al. |
| RE32,089 E | 3/1986 | Blatt et al. |
| 4,610,656 A | 9/1986 | Mortensen |
| 4,617,009 A | 10/1986 | Ohlin et al. |
| 4,627,879 A | 12/1986 | Rose et al. |
| 4,631,055 A | 12/1986 | Redl et al. |
| 4,632,761 A | 12/1986 | Bowers et al. |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger et al. |
| 4,714,457 A | 12/1987 | Alterbaum |
| 4,735,616 A | 4/1988 | Eibl et al. |
| 4,735,726 A | 4/1988 | Duggins |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers et al. |
| 4,844,818 A | 7/1989 | Smith |
| 4,846,835 A | 7/1989 | Grande |
| 4,850,952 A | 7/1989 | Figdor et al. |
| 4,853,137 A | 8/1989 | Ersson et al. |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani et al. |
| 4,902,281 A | 2/1990 | Avoy |
| 4,909,251 A | 3/1990 | Seelich et al. |
| 4,917,801 A | 4/1990 | Luderer et al. |
| 4,928,603 A | 5/1990 | Rose et al. |
| 4,929,242 A | 5/1990 | Desecki et al. |
| 4,939,081 A | 7/1990 | Figdor et al. |
| 4,943,273 A | 7/1990 | Pages et al. |
| 4,946,601 A | 8/1990 | Fiehler |
| 4,957,637 A | 9/1990 | Cornell |
| 4,957,638 A | 9/1990 | Smith |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |
| 5,024,613 A | 6/1991 | Vasconcellos et al. |
| 5,030,215 A | 7/1991 | Morse et al. |
| 5,030,341 A | 7/1991 | McEwen et al. |
| 5,045,048 A | 9/1991 | Kaleskas et al. |
| 5,047,004 A | 9/1991 | Wells |
| 5,053,127 A | 10/1991 | Schoendorfer et al. |
| 5,053,134 A | 10/1991 | Luderer et al. |
| 5,071,570 A | 12/1991 | Shiraki et al. |
| 5,080,262 A | 1/1992 | Herold et al. |
| 5,086,784 A | 2/1992 | Levine et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson et al. |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling et al. |
| 5,178,602 A | 1/1993 | Wells |
| 5,185,001 A | 2/1993 | Galanakis |
| 5,190,057 A | 3/1993 | Sarfarazi |
| 5,190,759 A | 3/1993 | Lindblad et al. |
| 5,197,985 A | 3/1993 | Caplan et al. |
| 5,203,825 A | 4/1993 | Haynes et al. |
| 5,204,537 A | 4/1993 | Bennet et al. |
| 5,206,023 A | 4/1993 | Hunziker et al. |
| 5,207,638 A | 5/1993 | Choksi et al. |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,226,914 A | 7/1993 | Caplan et al. |
| 5,234,608 A | 8/1993 | Duff |
| 5,236,604 A | 8/1993 | Fiehler |
| 5,251,786 A | 10/1993 | Sarrine |
| 5,258,126 A | 11/1993 | Pall et al. |
| 5,260,420 A | 11/1993 | Burnouf-Radosevich et al. |
| 5,269,927 A | 12/1993 | Fiehler |
| 5,271,852 A | 12/1993 | Luoma, II |
| 5,279,825 A | 1/1994 | Wehling et al. |

| | | |
|---|---|---|
| 5,281,342 A | 1/1994 | Biesel et al. |
| 5,290,552 A | 3/1994 | Sierra et al. |
| 5,290,918 A | 3/1994 | Bui-Khac et al. |
| 5,298,171 A | 3/1994 | Biesel et al. |
| 5,304,372 A | 4/1994 | Michalski et al. |
| 5,316,674 A | 5/1994 | Pall et al. |
| 5,318,524 A | 6/1994 | Morse et al. |
| 5,318,782 A | 6/1994 | Weis-Fogh et al. |
| 5,321,126 A | 6/1994 | van Dommelen et al. |
| 5,322,620 A | 6/1994 | Brown et al. |
| 5,330,974 A | 7/1994 | Pines et al. |
| 5,344,752 A | 9/1994 | Murphy |
| 5,370,802 A | 12/1994 | Brown |
| 5,376,263 A | 12/1994 | Fischel |
| 5,387,187 A | 2/1995 | Fell et al. |
| 5,393,674 A | 2/1995 | Levine et al. |
| 5,395,923 A | 3/1995 | Bui-Khac et al. |
| 5,403,272 A | 4/1995 | Deniega et al. |
| 5,405,607 A | 4/1995 | Epstein |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,474,687 A | 12/1995 | Van Vlasselaer |
| 5,486,359 A | 1/1996 | Caplan et al. |
| 5,494,578 A | 2/1996 | Brown et al. |
| 5,494,592 A | 2/1996 | Latham, Jr. et al. |
| 5,501,371 A | 3/1996 | Schwartz-Feldman |
| 5,505,685 A | 4/1996 | Antwiler |
| 5,510,102 A | 4/1996 | Cochrum |
| 5,533,518 A | 7/1996 | Vogler |
| 5,560,830 A | 10/1996 | Coleman et al. |
| 5,575,778 A | 11/1996 | Hardt et al. |
| 5,577,513 A | 11/1996 | Van Vlasselaer |
| 5,585,007 A | 12/1996 | Antanavich et al. |
| 5,588,958 A | 12/1996 | Cunningham et al. |
| 5,589,462 A | 12/1996 | Patat et al. |
| 5,601,727 A | 2/1997 | Bormann et al. |
| 5,607,579 A | 3/1997 | Latham, Jr. et al. |
| 5,614,106 A | 3/1997 | Payrat et al. |
| 5,618,663 A | 4/1997 | Delmas et al. |
| 5,632,895 A | 5/1997 | Tsukagoshi et al. |
| 5,632,905 A | 5/1997 | Haynes |
| 5,641,414 A | 6/1997 | Brown |
| 5,641,622 A | 6/1997 | Lake et al. |
| 5,643,192 A | 7/1997 | Hirsh et al. |
| 5,645,540 A | 7/1997 | Henniges et al. |
| 5,646,004 A | 7/1997 | Van Vlasselaer |
| 5,648,223 A | 7/1997 | Van Vlasselaer |
| 5,649,903 A | 7/1997 | Deniega et al. |
| 5,663,051 A | 9/1997 | Vlasselaer |
| 5,674,173 A | 10/1997 | Hlavinka et al. |
| 5,707,331 A | 1/1998 | Wells et al. |
| 5,707,647 A | 1/1998 | Dunn et al. |
| 5,707,876 A | 1/1998 | Levine |
| 5,716,616 A | 2/1998 | Prockop et al. |
| 5,723,331 A | 3/1998 | Tubo et al. |
| 5,724,988 A | 3/1998 | Dennehey et al. |
| 5,733,466 A | 3/1998 | Benebo et al. |
| 5,733,545 A | 3/1998 | Hood, III |
| 5,736,033 A | 4/1998 | Coleman et al. |
| 5,738,796 A | 4/1998 | Bormann et al. |
| 5,750,025 A | 5/1998 | Holmes et al. |
| 5,785,700 A | 7/1998 | Olson |
| 5,786,217 A | 7/1998 | Tubo et al. |
| 5,788,662 A | 8/1998 | Antanavich et al. |
| 5,795,489 A | 8/1998 | Holm et al. |
| 5,795,571 A | 8/1998 | Cederholm-Williams et al. |
| 5,795,751 A | 8/1998 | Apel |
| 5,811,094 A | 9/1998 | Caplan et al. |
| 5,811,151 A | 9/1998 | Hendriks et al. |
| 5,817,519 A | 10/1998 | Zelmanovic et al. |
| 5,823,986 A | 10/1998 | Peterson |
| 5,824,084 A | 10/1998 | Muschler |
| 5,830,359 A | 11/1998 | Knight et al. |
| 5,833,866 A | 11/1998 | Brown |
| 5,834,418 A | 11/1998 | Brazeau et al. |
| 5,837,150 A | 11/1998 | Langley et al. |
| 5,840,502 A | 11/1998 | Van Vlasselaer |
| 5,860,937 A | 1/1999 | Cohen |
| 5,863,892 A | 1/1999 | Stern et al. |
| 5,865,785 A | 2/1999 | Bischof |
| 5,889,584 A | 3/1999 | Wardlaw |
| 5,895,346 A | 4/1999 | Wells et al. |
| 5,899,874 A | 5/1999 | Jonsson et al. |
| 5,900,245 A | 5/1999 | Sawhney et al. |
| 5,906,934 A | 5/1999 | Grande et al. |
| 5,916,557 A | 6/1999 | Berlowitz-Tarrant et al. |
| 5,916,743 A | 6/1999 | Lake et al. |
| 5,918,622 A | 7/1999 | Perez et al. |
| 5,924,972 A | 7/1999 | Turvaville et al. |
| 5,934,803 A | 8/1999 | Hutter |
| 5,938,621 A | 8/1999 | Kelly et al. |
| 5,955,032 A | 9/1999 | Kelly et al. |
| 5,955,436 A | 9/1999 | Kunkle, Jr. |
| 5,958,250 A | 9/1999 | Brown et al. |
| 5,958,253 A | 9/1999 | Holm et al. |
| 5,980,734 A | 11/1999 | Itoh et al. |
| 6,010,627 A | 1/2000 | Hood, III |
| 6,022,306 A | 2/2000 | Dumont et al. |
| 6,025,201 A | 2/2000 | Zelmanovic et al. |
| 6,027,655 A | 2/2000 | Holm et al. |
| 6,049,026 A | 4/2000 | Muschler |
| 6,051,146 A | 4/2000 | Green et al. |
| 6,051,147 A | 4/2000 | Bischof |
| 6,053,856 A | 4/2000 | Hlavinka |
| 6,054,122 A | 4/2000 | MacPhee et al. |
| 6,063,297 A | 5/2000 | Antanavich et al. |
| 6,063,624 A | 5/2000 | Kandler et al. |
| 6,071,421 A | 6/2000 | Brown |
| 6,071,422 A | 6/2000 | Hlavinka et al. |
| 6,071,423 A | 6/2000 | Brown et al. |
| 6,090,793 A | 7/2000 | Zimmermann et al. |
| 6,096,309 A | 8/2000 | Prior et al. |
| 6,117,425 A | 9/2000 | MacPhee et al. |
| 6,123,655 A | 9/2000 | Fell et al. |
| 6,150,163 A | 11/2000 | McPherson et al. |
| 6,153,113 A | 11/2000 | Goodrich et al. |
| 6,183,737 B1 | 2/2001 | Zaleske et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,200,606 B1 | 3/2001 | Peterson et al. |
| 6,214,338 B1 | 4/2001 | Antanavich et al. |
| 6,221,315 B1 | 4/2001 | Giesler et al. |
| 6,245,900 B1 | 6/2001 | Yamasaki et al. |
| 6,264,890 B1 | 7/2001 | Boehringer et al. |
| 6,274,090 B1 | 8/2001 | Coelho et al. |
| 6,277,961 B1 | 8/2001 | Hock et al. |
| 6,280,400 B1 | 8/2001 | Niermann |
| 6,296,602 B1 | 10/2001 | Headley |
| 6,316,247 B1 | 11/2001 | Katz et al. |
| 6,322,785 B1 | 11/2001 | Landesberg et al. |
| 6,327,491 B1 | 12/2001 | Franklin et al. |
| 6,328,765 B1 | 12/2001 | Hardwick et al. |
| 6,342,157 B1 | 1/2002 | Hood, III |
| 6,351,659 B1 | 2/2002 | Vilsmeier et al. |
| 6,355,239 B1 | 3/2002 | Bruder et al. |
| 6,368,298 B1 | 4/2002 | Beretta et al. |
| 6,398,972 B1 | 6/2002 | Blasetti et al. |
| 6,406,671 B1 | 6/2002 | DiCesare et al. |
| 6,410,344 B1 | 6/2002 | Chung et al. |
| 6,417,004 B1 | 7/2002 | Brady et al. |
| 6,440,444 B2 | 8/2002 | Boyce et al. |
| 6,444,228 B1 | 9/2002 | Baugh et al. |
| 6,472,162 B1 | 10/2002 | Coelho et al. |
| 6,508,778 B1 | 1/2003 | Verkaart et al. |
| 6,516,953 B1 | 2/2003 | DiCesare et al. |
| 6,523,698 B1 | 2/2003 | Dennehey et al. |
| 6,544,162 B1 | 4/2003 | Van Wie et al. |
| 6,558,341 B1 | 5/2003 | Swisher |
| 6,596,180 B2 | 7/2003 | Baugh et al. |
| 6,629,919 B2 | 10/2003 | Egozy et al. |
| 6,676,629 B2 | 1/2004 | Andrew et al. |
| 6,719,901 B2 | 4/2004 | Dolecek et al. |

| | | |
|---|---|---|
| 6,733,471 B1 | 5/2004 | Ericson et al. |
| 6,758,978 B1 | 7/2004 | Bedell |
| 6,777,231 B1 | 8/2004 | Katz et al. |
| 6,803,022 B2 | 10/2004 | DiCesare et al. |
| 6,811,777 B2 | 11/2004 | Mishra |
| 6,835,377 B2 | 12/2004 | Goldberg et al. |
| RE38,730 E | 4/2005 | Wells et al. |
| 6,899,813 B2 | 5/2005 | Dolecek et al. |
| 6,905,612 B2 | 6/2005 | Dorian et al. |
| 6,911,202 B2 | 6/2005 | Amir et al. |
| RE38,757 E | 7/2005 | Wells et al. |
| 7,011,644 B1 | 3/2006 | Andrew et al. |
| 7,077,273 B2 | 7/2006 | Ellsworth et al. |
| 7,077,827 B2 | 7/2006 | Greenfield |
| 7,179,391 B2 | 2/2007 | Leach et al. |
| 7,195,606 B2 | 3/2007 | Ballin |
| 7,223,346 B2 | 5/2007 | Dorian et al. |
| 7,374,678 B2 | 5/2008 | Leach et al. |
| 7,470,371 B2 | 12/2008 | Dorian et al. |
| 7,553,413 B2 | 6/2009 | Dorian et al. |
| 2001/0009757 A1 | 7/2001 | Bischof et al. |
| 2002/0035820 A1 | 3/2002 | Farris |
| 2002/0076400 A1 | 6/2002 | Katz et al. |
| 2002/0082220 A1 | 6/2002 | Hoemann et al. |
| 2002/0090711 A1 | 7/2002 | Karlsson |
| 2002/0104808 A1 | 8/2002 | Blasetti et al. |
| 2002/0114775 A1 | 8/2002 | Pathak |
| 2002/0161449 A1 | 10/2002 | Muschler |
| 2002/0169408 A1 | 11/2002 | Beretta et al. |
| 2002/0172666 A1 | 11/2002 | Sacchi et al. |
| 2002/0182664 A1 | 12/2002 | Dolecek et al. |
| 2003/0033021 A1 | 2/2003 | Plouhar et al. |
| 2003/0033022 A1 | 2/2003 | Plouhar et al. |
| 2003/0050709 A1 | 3/2003 | Noth et al. |
| 2003/0050710 A1 | 3/2003 | Petersen et al. |
| 2003/0082152 A1 | 5/2003 | Hedrick et al. |
| 2003/0185803 A1 | 10/2003 | Kadiyala et al. |
| 2003/0191429 A1 | 10/2003 | Andrew et al. |
| 2003/0205538 A1 | 11/2003 | Dorian et al. |
| 2004/0120942 A1 | 6/2004 | McGinnis et al. |
| 2004/0171146 A1 | 9/2004 | Katz et al. |
| 2004/0182395 A1 | 9/2004 | Brookman |
| 2004/0182788 A1 | 9/2004 | Dorian et al. |
| 2004/0182795 A1 | 9/2004 | Dorian et al. |
| 2005/0076396 A1 | 4/2005 | Katz et al. |
| 2005/0084961 A1 | 4/2005 | Hedrick et al. |
| 2005/0084962 A1 | 4/2005 | Simon |
| 2005/0109716 A1 | 5/2005 | Leach et al. |
| 2005/0130301 A1 | 6/2005 | McKay et al. |
| 2005/0153441 A1 | 7/2005 | Hedrick et al. |
| 2005/0153442 A1 | 7/2005 | Katz et al. |
| 2005/0186120 A1 | 8/2005 | Dorian et al. |
| 2005/0196874 A1 | 9/2005 | Dorian et al. |
| 2005/0260174 A1 | 11/2005 | Fraser et al. |
| 2005/0260175 A1 | 11/2005 | Hedrick et al. |
| 2005/0282275 A1 | 12/2005 | Katz et al. |
| 2006/0051865 A1 | 3/2006 | Higgins et al. |
| 2006/0057693 A1 | 3/2006 | Simon |
| 2006/0083720 A1 | 4/2006 | Fraser et al. |
| 2006/0151384 A1* | 7/2006 | Ellsworth et al. ............ 210/518 |
| 2006/0175242 A1 | 8/2006 | Dorian et al. |
| 2006/0175244 A1 | 8/2006 | Dorian et al. |
| 2006/0196885 A1 | 9/2006 | Leach et al. |
| 2006/0243676 A1 | 11/2006 | Swift et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0034579 A1 | 2/2007 | Dorian et al. |
| 2007/0036768 A1 | 2/2007 | Fraser et al. |
| 2007/0075016 A1 | 4/2007 | Leach |
| 2007/0208321 A1 | 9/2007 | Leach et al. |
| 2008/0011684 A1 | 1/2008 | Dorian et al. |
| 2008/0193424 A1 | 8/2008 | McKale et al. |
| 2008/0217263 A1 | 9/2008 | Higgins et al. |
| 2008/0217264 A1 | 9/2008 | Leach et al. |
| 2008/0217265 A1 | 9/2008 | Leach et al. |
| 2008/0268064 A1 | 10/2008 | Woodell-May |
| 2008/0269762 A1 | 10/2008 | Simon et al. |
| 2008/0283474 A1 | 11/2008 | Leach et al. |
| 2008/0306431 A1 | 12/2008 | Yoo |
| 2009/0101599 A1 | 4/2009 | Dorian et al. |
| 2009/0192528 A1 | 7/2009 | Higgins et al. |
| 2009/0220482 A1 | 9/2009 | Higgins et al. |
| 2009/0221075 A1 | 9/2009 | Dorian et al. |
| 2009/0236297 A1 | 9/2009 | Dorian et al. |
| 2009/0250413 A1 | 10/2009 | Hoeppner |
| 2009/0253566 A1 | 10/2009 | Chavarria |
| 2010/0055087 A1 | 3/2010 | Higgins et al. |

FOREIGN PATENT DOCUMENTS

| | | |
|---|---|---|
| BR | 9103724 | 3/1993 |
| CA | 1321138 | 8/1993 |
| CA | 2182862 | 6/1996 |
| CN | 1074709 | 7/1993 |
| DE | 1443359 | 11/1968 |
| EP | 090997 | 10/1983 |
| EP | 0102773 | 3/1984 |
| EP | 0109374 | 5/1984 |
| EP | 0142339 | 5/1985 |
| EP | 0244834 | 11/1987 |
| EP | 0253198 | 1/1988 |
| EP | 0295771 | 12/1988 |
| EP | 0417818 | 3/1991 |
| EP | 0534178 | 3/1993 |
| EP | 534178 | 3/1993 |
| EP | 0592242 | 4/1994 |
| EP | 1005910 | 6/2000 |
| EP | 1006360 | 6/2000 |
| EP | 1289618 | 3/2003 |
| EP | 1427279 A1 | 6/2004 |
| EP | 1467746 A2 | 10/2004 |
| EP | 1509326 | 3/2005 |
| EP | 1670315 A2 | 6/2006 |
| EP | 1716901 | 11/2006 |
| GB | 854715 | 11/1960 |
| JP | 60-053845 | 3/1985 |
| JP | 60250014 | 12/1985 |
| JP | 2036872 | 2/1990 |
| JP | 02071747 | 3/1990 |
| JP | 02129224 | 10/2000 |
| WO | WO-8400905 | 3/1984 |
| WO | WO-8802259 | 4/1988 |
| WO | WO-9010031 | 9/1990 |
| WO | WO-9222312 | 12/1992 |
| WO | WO-9305067 | 3/1993 |
| WO | WO-9308904 | 5/1993 |
| WO | WO-9407548 | 4/1994 |
| WO | WO-9617871 | 6/1996 |
| WO | WO-0061256 | 10/2000 |
| WO | WO-0103756 | 1/2001 |
| WO | WO-0183068 | 11/2001 |
| WO | WO-0238610 | 5/2002 |
| WO | WO-02060925 | 8/2002 |
| WO | WO-03015800 | 2/2003 |
| WO | WO-03024215 A1 | 3/2003 |
| WO | WO-03053362 A2 | 7/2003 |
| WO | WO-03088905 | 10/2003 |
| WO | WO-03092894 | 11/2003 |
| WO | WO-03099412 | 12/2003 |
| WO | WO-2004009207 | 1/2004 |
| WO | WO-2004104553 | 12/2004 |
| WO | WO-2005034843 A2 | 4/2005 |
| WO | WO-2007142908 A1 | 12/2007 |

OTHER PUBLICATIONS

International Search Report for International Application No. PCT/US2007/012587 mailed Nov. 6, 2007 which claims benefit of U.S. Appl. No. 11/441,276, filed May 25, 2006.

Written Opinion of the International Preliminary Examining Authority mailed Mar. 17, 2009 for International Application No. PCT/US2008/004687 which claims priority to U.S. Appl. No. 60/911,407, filed Apr. 12, 2007.

Anesthesiology, vol. 81, No. 4, pp. 1074-1077, Oct. 1994, Hiromasa Mitsuhata, M.D., et al., "An Anaphylactic Reaction to Topical Fibrin Glue".

Ann Thorac Surg, vol. 53, pp. 530-531, 1992, Mehmet C. Oz, M.D., et al., "Autologous Fibrin Glue From Intraoperatively Collected Platelet-Rich Plasma".

Ann Thorac Surg, vol. 56, pp. 387-389, 1993, Robert L. Quigley, M.D., et al., "Intraoperative Procurement of Autologous Fibrin Glue".

Bang, N. U., et al., "Plasma Protein Requirements for Human Platelet Aggregation" Ann. N.Y. Acad Sci, 201:280-299 (1972).

Berguer, R., R. L. Staerkel, E. E. Moore, F. A. Moore, W. B. Galloway, and M. B. Mockus. "Warning: fatal reaction to the use of fibrin glue in deep hepatic wounds. Case reports." *J Trauma* 31 (Mar. 1991): 408-11.

Berruyer, M., J. Amiral, P. Ffrench, J. Belleville, O. Bastien, J. Clerc, A. Kassir, S. Estanove, and M. Dechavanne. "Immunization by bovine thrombin used with fibrin glue during cardiovascular operations. Development of thrombin and factor V inhibitors," *J Thorac Cardiovasc Surg* 105 (May 1993): 892-7.

Biopolymers, vol. 27, pp. 763-774, 1988, Gerald Marx, "Mechanism of Fibrin Coagulation Based on Selective, Cation-Driven, Protofibral Association".

Brodke, et al., "Bone Grafts Prepared with Selective Cell Retention Technology Heal Canine Segmental Defects as Effectively as Autograft", SCR-Enriched Bone Crafts Heal Canine Segmental Defects, Journal of Orthopaedic Research (May 2006) pp. 857-866.

Casali, B., F. Rodeghiero, A. Tosetto, B. Palmieri, R. Immovilli, C. Ghedini, and P. Rivasi. "Fibrin glue from single-donation autologous plasmapheresis." Transfusion 32 (Jul. 1992): 641-3.

Clotalyst™ Automatic Clotting Factor, Would you like to have an autologous thrombin for rapid clotting and haemostasis?, brochure, Biomet Biologics, Inc., Feb. 2007 (12 pages).

Collier, B.S. et al., "The pH Dependence of Quantitative Ristocetin-induced Platelet Aggregation: Theoretical and Practical Implications—A New Device for Maintenance of Platelet-Rich Plasma pH", Hematology Service, Clinical Pathology Department, Clinical Center, National Institutes of Health, Bethesda, Md. 20014, Blood, vol. 47, No. 5 (May), 1976.

Dallari, et al., "In Vivo Study on the Healing of Bone Defects Treated with Bone Marrow Stromal Cells, Platelet-Rich Plasma, and Freeze-Dried Bone Allografts, Alone and in Combination," Healing of Bone Defects, Journal of Orthopaedic Research (May 2006) pp. 877-888.

DelRossi, A. J., A. C. Cernaianu, R. A.Vertrees, C. J. Wacker, S. J. Fuller, J. Cilley Jr., and W. A. Baldino. "Platelet-rich plasma reduces postoperative blood loss after cardiopulmonary bypass." *J Thorac Cardiovasc Surg* 100 (Feb. 1990): 281-6.

Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".

Edlich, Richard F., George T. Rodeheaver, and John G. Thacker. "Surgical Devices in Wound Healing Management." In *Wound Healing: Biochemical & Clinical Aspects*, ed. I. Kelman Cohen, Robert F. Diegelmann, and William J. Lindblad. 581-600. 1st ed., Vol. Philadelphia: W.B. Saunders Company, 1992).

Epstein, G. H., R. A. Weisman, S. Zwillenberg, and A. D. Schreiber. "A new autologous fibrinogen-based adhesive for otologic surgery." *Ann Otol Rhinol Laryngol* 95 (1 Pt 1 1986): 40-5.

Fibrostik™ Plasma Concentrator, Attention Operating Surgeon, Cell Factor Technologies, Inc., Jul. 2003.

First clinical results: Kuderma, H. and Helene Matras. "Die klinische Anwendung der Klebung van Nervenanastomosen mit Gerinnungssubstanzen bei der Rekonstruction verletzter peripherer Nerven." Wein Klin Wochenschr 87 (15 1975): 495-501.

Galois, et al., "Cartilage Tissue Engineering: State-of-the-Art and Future Approaches," Pathol Biol (Paris), 53(10), Dec. 2005.

Gibble, J. W. and P. M. Ness. "Fibrin glue: the perfect operative sealant?" *Transfusion* 30 (Aug. 1990): 741-7.

GPS® III System, GPS® III Platelet Separation System, Leadership through Technology, brochure, Jul. 2007 (8 sheets).

GPS® System, "GPS® Platelet Concentrate System," Cell Factor Technologies, Inc., Biomet Orthopaedics, Inc., (2004) (9 pages).

GPS® System, "Shoulder Recovery with the GPS® Platelet Concentrate System, Rotator Cuff Surgical Techniques," brochure, Cell Factor Technologies, Inc., Biomet Orthopaedics, Inc., (2004) 6 pages.

GPS® System, "Shoulder Recovery with the GPS® Platelet Concentrate System, Rotator Cuff Surgical Techniques," Cell Factor Technologies, Inc., Biomet Orthopaedics, Inc., (2004) 3 pages, http://www.cellfactortech.com/global_products.cfm, printed Sep. 16, 2005.

GPS®II System, Gravitational Platelet Separation System, "Accelerating the Body's Natural Healing Process," Cell Factor Technologies, Inc., Biomet Europe (2005) 16 pages, http://www.cellfactortech.com/global_products.cfm, printed Sep. 16, 2005.

GPS®II System, Gravitational Platelet Separation System, "User Manual," Cell Factor Technologies, Inc., Biomet Europe [date unknown] 13 pages, http://www.cellfactortech.com/global_products.cfm, printed Sep. 16, 2005.

Grove, et al., "Plasticity of Bone Marrow-Derived Stem Cells," Stem Cells: Concise Review, 22, Jan. 2004.

Harris, E.L.V. Concentration of the Extract. In. Protein Purification Methods: A Practical Approach Harris, E.L.V.; Angal, S.; Editors. (1989) Publisher: (IRL Press, Oxford, UK), pp. 67-69.

Hartman, A. R., D. K. Galanakis, M. P. Honig, F. C. Seifert, and C. E. Anagnostopoulos. "Autologous whole plasma fibrin gel. Intraoperative procurement." *Arch Surg* 127 (Mar. 1992): 357-9.

Harvest Technologies brochure, SmartPrep2 (2002).

Hennis, H. L., W. C. Stewart, and E. K. Jeter. "Infectious disease risks of fibrin glue [letter]." *Ophthalmic Surg* 23 (Sep. 1992): 640.

Jackson, C. M. and Y. Nemerson. "Blood coagulation." *Annu Rev Biochem* 49 (811 1980): 765-11).

Jorgensen, et al., "Stem Cells for Repair of Cartilage and Bone: The Next Challenge in Osteoarthritis and Rheumatoid Arthritis," Annals of Rheumatic Diseases, Aug. 2000.

Journal of Biomaterials Applications, vol. 7, pp. 309-353, Apr. 1993, David H. Sierra, "Fibrin Sealant Adhesive Systems: A review of their Chemistry, Material Properties and Clinical Appllications".

Journal of Oral Maxillofacial Surgery, vol. 43, pp. 605-611, 1985, Helene Matras, M.D., "Fibrin Seal: The State of the Art".

Karpatkin, S., "Heterogeneity of Human Platelets. VI., Correlation of Platelet Function with Platelet Volume", Blood, vol. 51, No. 2 (Feb. 1978).

Kjaergard, H. K,, U. S. Weis-Fogh, H. Sorensen, J. Thiis, and I. Rygg. "A simple method of preparation of autologous fibrin glue by means of ethanol." *Surg Gynecol Obstet* 175 (Jan. 1992): 72-3.

Kjaergard, H. K., Fogh Us Weis, and J. J. Thiis. "Preparation of autologous fibrin glue from pericardial blood." *Ann Thorac Sur* 55 (Feb. 1993): 543-4.

Laryngoscope vol. 99, pp. 974-976, Sep. 1989, Kyosti Laitakari, M.D., et al., "Autologous and Homologous Fibrinogen Sealants: Adhesive Strength".

Laryngoscope, vol. 95, pp. 1074-1076, Sep. 1985, Karl H. Siedentop, M.D., et al., "Autologous Fibrin Tissue Adhesive".

Laryngoscope, vol. 96, pp. 1062-1064, Oct. 1986, Karl H. Siedentop, M.D., et al., "Extended Experimental and Preliminary Surgical Findings with Autologous Fibrin Tissue Adhesive Made from Patient's Own Blood".

Lasher, Lisa, M.D., "My Experience with PRP," PowerPoint presentation, http://www.cellfactortech.com/global_products.cfm, printed Sep. 16, 2005.

Lerner, R. and N. S. Binur. "Current status of surgical adhesives." *J Suri Res* 48 (Feb. 1990): 165-81.

Lu, et al., "Bone Marrow Mesenchymal Stem Cells: Progress in Bone/Cartilage Defect Repair," 19(1), Jan. 2002.

Matras, Helene, H. P. Dinges, H. Lassmann, and B. Mamoli. "Zur nahtlosen interfaszikularen Nerventransplantation im Tierexperiment." Wein Med Woschtr 122 (37 1972): 517-523.

Minntech® Filtration Technologies Group, "Hemocor HPH® Hemoconcentrator," Minntech Corporation (2004); http://www.minntech.com/ftg/products/hph/index.html, printed Jul. 15, 2004 (2 pages).

Minntech® Filtration Technologies Group, "Medical Applications: Blood Filtration" Minntech Corporation (2004); http://www.minntech.com/ftg/industries/medical/blood_filter.html, printed Jul. 15, 2004 (1 page).

Minntech® Filtration Technologies Group, "Medical Applications: Blood Filtration" Minntech Corporation (2004); http://www.minntech.com/ftg/industries/medical/blood_filter.html, printed Jul. 15, 2004 (1 page).

Minntech® Filtration Technologies Group, "Renaflo® II Hemofilter," Minntech Corporation (2004); http://www.minntech.com/ftg/products/renaflo/index.html, printed Jul. 15, 2004 (2 pages).

Molnar, Amy, "Stem Cells from Muscles Can Repair Cartilage, Study Finds Genetically Engineered Muscle-Derived Stem Cells Improved Cartilage Repair in Rats", American College of Rheumatology, (2005).

Moretz, W., Jr., J Shea Jr., J. R. Emmett, and J Shea. "A simple autologous fibrinogen glue for otologic surgery." *Otolaryngol Head Neck Surg* 95 (Jan. 1986): 122-4.

Nilsson, et al., "Bone Repair Induced by Bone Morphogenetic Protein in Ulnar Defects in Dogs," The Journal of Bone and Joint Surgery, vol. 68 B., No. 4, Aug. 1986.

Otolaryngologic Clinics of North America, vol. 27, No. 1, pp. 203-209, Feb. 1994, Dean M. Toriumi, M.D., et al., "Surgical Tissue Adhesives in Otolaryngology-Head and Neck Surgery".

Ponticiello, Michael S., "A Rapid Technique for the Isolation and Concentration of Stem Cells from Human Bone Marrow", Cell Factor Technologies, Inc. (undated) 1 page.

Sanal, M. "Does fibrin glue cause foreign body reactions? [letter]." *Eur J Pediatr Surg* 3 (Mar. 1993): 190 (1 page).

Sanal, M., H. Dogruyol, A. Gurpinar, and O. Yerci. "Does fibrin glue cause foreign body reactions?" *Eu r J Pediatr Surg* 2 (May 1992): 285-6.

Schmidt, K.G., et al., "Labelling of Human and Rabbit Platelets with Indium-Oxine Complex", 23:97-106 (1979).

Schmidt, K.G., et al., "Preparation of Platelet Suspensions from Whole Blood in Buffer", Scand. J. Hoemato, 23:88-96 (1979).

Siedentop, K. H., D. M. Harris, and B. Sanchez. "Autologous fibrin tissue adhesive." *Laryngoscope* 95 (9 Pt 1 1985): 1074-6.

Sierra, D. H. "Fibrin sealant adhesive systems: a review of their chemistry, material properties and clinical applications." *J Biomater Appl* 7 (Apr. 1993): 309-52.

Swift, Mathew J., et al., "Characterization of Growth Factors in Platelet Rich Plasma," 1-Cell Factor Technologies, http://www.cellfactortech.com/global_products.cfm, printed Sep. 16, 2005.

Symphony II Platelet Concentrate System/PCS brochure; "Increasing bone graft bioactivity through reproducible concentrations of natural growth factors," DePuy (Jan. 2003).

The American Journal of Surgery, vol. 168, pp. 120-122, Aug. 1994, Roy L. Tawes, Jr., M.D., et al., "Autologous Fibrin Glue: The Last Step in Operative Hemostatis".

The American Surgeon, vol. 55, pp. 166-168, Mar. 1989, William D. Spotnitz, M.D., et al., "Successful Use of Fibrin Glue During 2 Years of Surgery at a University Medical Center".

The Sports Medicine Center, "Knee Cartilage Implantation", Carticel™, "Autologous Cultured Chondrocyte Implantation", http://www.orthoassociates.com/carticel.htm (printed Apr. 6, 2006).

The Stone Clinic, "Platelet Rich Plasma (PRP)", web site printed May 2006.

Thompson, D.F., Letassy, N. A.., and Thompson, G. D., Fibrin "Glue: a review of its preparation, efficacy, and adverse effects as a topical hemostat." *Drug Intell Clin Pharm*, 1988. 22(12): p. 946-52.

Transfusion, vol. 30, No. 8, pp. 741-747, 1990, J.W. Gibble, et al., "Fibrin Glue: The Perfect Operative Sealant?".

Vox Sanquinis, vol. 68: 82-89, Feb. 1995, Boomgaard et. al, Pooled Platelet Concentration Prepred by the . . . .

Weis-Fogh, U. S. "Fibrinogen prepared from small blood samples for autologous use in a tissue adhesive system." *Eur Surg* Res 20 (May-Jun. 1988): 381-9.

Wiseman, David M., David T. Rovee, and Oscar M. Alverez "Wound Dressings: Design and Use." In *Wound Healing: Biochemical & Clinical Aspects*,ed. I. Kelman Cohen, Robert F. Diegelmann, and William J. Lindblad. 562-580. 1st ed., Vol. Philadelphia: W. B. Saunders Company, 1992).

International Search Report for International Application No. PCT/US/0316506 mailed Oct. 13, 2003.

International Search Report and Written Opinion mailed Jul. 2, 2008 for International Application No. PCT/US2008/004687.

Badiavas, et al., "Treatment of Chronic Wounds With Bone Marrow-Derived Cells," (Reprinted) Arch Dermatol. 139:510-516 (Apr. 2003).

Connolly, "Injectable Bone Marrow Preparations to Stimulate Osteogenic Repair," Clinical Orthopaedics and Related Research 313:8-18 (1995).

De Ugarte, et al., "Comparison of Multi-Lineage Cells from Human Adipose Tissue and Bone Marrow," Cells Tissues Organs 174:101-109 (2003).

De Ugarte, et al., "Differential Expression of Stem Cell Mobilization-Associated Molecules on Multi-Lineage Cells from Adipose Tissue and Bone Marrow," Immunology Letters 89:267-270 (2003).

Eppley, et al., "Platelet Quantification and Growth Factor Analysis from Platelet-Rich Plasma: Implications for Wound Healing," Plastic and Reconstructive Surgery, 114(6):1502-1508 (Nov. 2004).

Floryan, K. et al. "Home Study Program: Intraoperative Use of Autologous Platelet-Rich and Platelet-Poor Plasma for Orthopedic Surgery Patients" vol. 80, No. 4 (Oct. 2004) p. 667-674.

Haynesworth, S.E. et al. "Mitogenic Stimulation of Human Mesenchymal Stem Cells by Platelet Releasate Suggests a Mechanism for Enhancement of Bone Repair by Platelet Concentrate" 48th Annual Meeting of the Orthopaedic Research Society Poster No. 0462 (2002).

Hernigou, et al., "Percutaneous Autologous Bone-Marrow Grafting for Nonunions. Influence of the Number and Concentration of Progenitor Cells," Journal of Bone & Joint Surgery, 87-A(7):1430-1437 (Jul. 2005).

International Preliminary Examination Report and Written Opinion issued Aug. 31, 2010 for PCT/US2009/035564 claiming benefit of U.S. Appl. No. 61/078,178, filed Jul. 3, 2008, which priority is also claimed of said provisional case by U.S. Appl. No. 12/395,085, filed Feb. 27, 2009.

International Search Report and Written Opinion mailed Jul. 30, 2010 for PCT/US2010/029957 which claims benefit of U.S. Appl. No. 12/417,789, filed Apr. 3, 2009.

Ishida, et al., "Platelet-Rich Plasma With Biodegradable Gelatin Hydrogel Promotes Rabbit Meniscal Tissue Regeneration," 52nd Annual Meeting of the Orthopaedic Research Society Paper No. 1035, 1 page (2006).

Johnstone, et al., "Autologous Mesenchymal Progenitor Cells in Articular Cartilage Repair", Clinical Orthopaedics and Related Research 367S:S156-S162 (1999).

Marrowstim Concentration System, Biomet Biologics, Inc., 20 pages (REV Feb. 15, 2008).

Woodell-May, et al., "Producing Accurate Platelet Counts for Platelet Rich Plasma: Validation of a Hematology Analyzer and Preparation Techniques for Counting," Scientific Foundation, Journal of Carniofacial Surgery 16(5):749-756 (Sep. 2005).

"Cell Isolation Techniques, Methods and Materials, Working with Enzymes," (2004) (9 pages) Worthington Biochemical Corp.

"Cell Isolation Theory, Tissue Types," (2004) (5 pages) Worthington Biochemical Corp.

"Cytori Celution Cell Concentrate Device," Exhibit 14, 510(k) Summary, FDA approval K060482 (Sep. 28, 2006).

"Frequently Asked Questions, 1. Kits, 2. Engzymes," (2003) 3 pages Worthington Biochemical Corp.

DeUgarte, M.D., Daniel A., et al., "Future of Fat as Raw Material for Tissue Regneration," (2007) pp. 215-219, Lippincott Williams & Wilkins, Inc.

DiMuzio, Paul et al., "Development of a Tissue-Engineered Bypass Graft Seeded with Stem Cells," Vasucular, vol. 14, No. 6, (2006) pp. 338-342, BC Decker, Inc.

Frasier, John K., et al., "Plasticity of human adipose stem cells toward endothelial cells and cardiomyocytes," Nature Clinical Practice Cardiovascular Medicine, vol. 3, Supplement 1 (Mar. 2006) pp. S33-S37.

Gimble, Jeffrey M., "Adipose-Derived Stem Cells for Regenerative Medicine," Circulation Research (2007) pp. 1249-1260, American Heart Association, Inc.

Gomillion, Cheryl T., et al., "Stem cells and adipose tissue engineering," Biomaterials 27, Science Direct (2006) pp. 6052-6063, Elsevier.

Guilak, Frank, et al., "Adipose-derived adult stem cells for cartilage tissue engineering," Biorheology 41 (2004) pp. 389-399, IOS Press.

Hattori, et al., "Osteogenic Potential of Human Adipose Tissue-Derived Stromal Cells as an Alternative Stem Cell Source," Cells Tissues Organs (2004) 178:2-12 Karger.

International Preliminary Report on Patentability completed Aug. 13, 2009 for PCT/US2008/004687 claiming benefit of U.S. Appl. No. 60/911,407, filed Apr. 12, 2007.

International Search Report and Written Opinion mailed Jul. 3, 2009 for PCT/US2009/035564 claiming benefit of U.S. Appl. No. 61/078,178, filed Jul. 3, 2008.

Lendeckel, Stefan, et al., "Autologous stem cells (adipose) and fibrin glue used to treat widespread traumatic calvarial defects: case report," Journal of Cranio-Maxillofacial Surgery (2004) European Association for Cranio-Maxillofacial Surgery.

Nakagami, Hironori, et al., "Novel Autologous Cell Tehrapy in Ischemic Limb Disease Through Growth Factor Secretion by Cultured Adipose Tissue-Derived Stromal Cells," Angiogenesis by Adipose Tissue-Derived Cells, (2005) pp. 2542-2547, American Heart Association, Inc.

Nathan, Suresh,, et al., "Cell-Based Therapy in the Repair of Osteochondral Defects: A Novel Use for Adipose Tissue," Tissue Engineering, vol. 9, No. 4 (2003) pp. 733-744 Mary Ann Liebert, Inc.

Parker, Anna M., et al., Adipose-derived stem cells for the regeneration of damaged tissues, Expert Opinion, Cell- & Tissue-based Therapy, Expert Opin. Biol. Ther. (2006) pp. 567-578 Informa UK Ltd.

Planat-Bénard, V., et al., "Spontaneous Cardiomyocyte Differentiation From Adipose Tissue Stroma Cells," Adipose-Derived Cell Cardiomyocyte (2004) pp. 223-229 American Heart Association, Inc.

Rangappa, Sunil, M.D., "Transformation of Adult Mesenchymal Stem Cells Isolated From the Fatty Tissue Into Cardiomyocytes," Adult Stem Cells Transformed into Cardiomyoctyes, (2003) pp. 775-779 Ann Thorac Surg.

Rigotti, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Breast, PRS Journal vol. 119, No. 5, Stem Cell Therapy for Angiogenesis, (Pub. 2005) pp. 1409-1422.

Rubin, M.D., et al, "Clinical Treatment of Radiotherapy Tissue Damage by Lipoaspirate Transplant: A Healing Process Mediated by Adipose-Derived Adult Stem Cells," Plastic and Reconstructive Surgery, Discussion vol. 119, No. 5, Stem Cell Therapy for Angiogenesis, (2007) pp. 1423-1424.

Schäffler, Andreas, et al., "Concise Review: Adipose Tissue-Derived Stromal Cells—Basic and Clinical Implications for Novel Cell-Based Therapies," Tissue-Specific Stem Cells, Stem Cells® (2007) pp. 818-827 AlphaMed Press.

Sigma-Aldrich® Alkaline Phosphatase (Procedure No. 85), drug fact sheet, (2003) pp. 1-2, Sigma-Aldrich, Inc.

Takahashi, Kazutoshi et al., "Induction of Pluripotent Stem Cells from Adult Human Fibroblasts by Defined Factors," Cell, (2007) pp. 1-12, Elsevier Inc.

Yoon, Eulsik, M.D., Ph.D., et al., "In Vivo Osteogenic Potential of Human Adipose-Derived Stem Cells/Poly Lactide-Co-Glycolic Acid Constructs for Bone Regneration in a Rat Critical-Sized Calvarial Defect Model," Tissue Engineering, vol. 13, No. 3 (2007) pp. 619-627 Mary Ann Liebert, Inc.

Zhang, Duan-zhen, et al., "Transplantation of autologous adipose-derived stem cells ameliorates cardiac function in rabbits with myocardial infarction," Chinese Medical Journal, vol. 120, No. 4 (2007) pp. 300-307 General Hospital of Shenyang Military Region, Shenyang, China.

Zuk, Patricia A., Ph.D., "Multilineage Cells from Human Adipose Tissue: Implications for Cell-Based Therapies," Tissue Engineering, vol. 7, No. 2, (2001) pp. 211-228 Mary Ann Liebert, Inc.

Office Action mailed Nov. 16, 2010 for U.S. Appl. No. 12/897,401 claiming benefit of U.S. Appl. No. 12/101,594, filed Apr. 11, 2008.

* cited by examiner

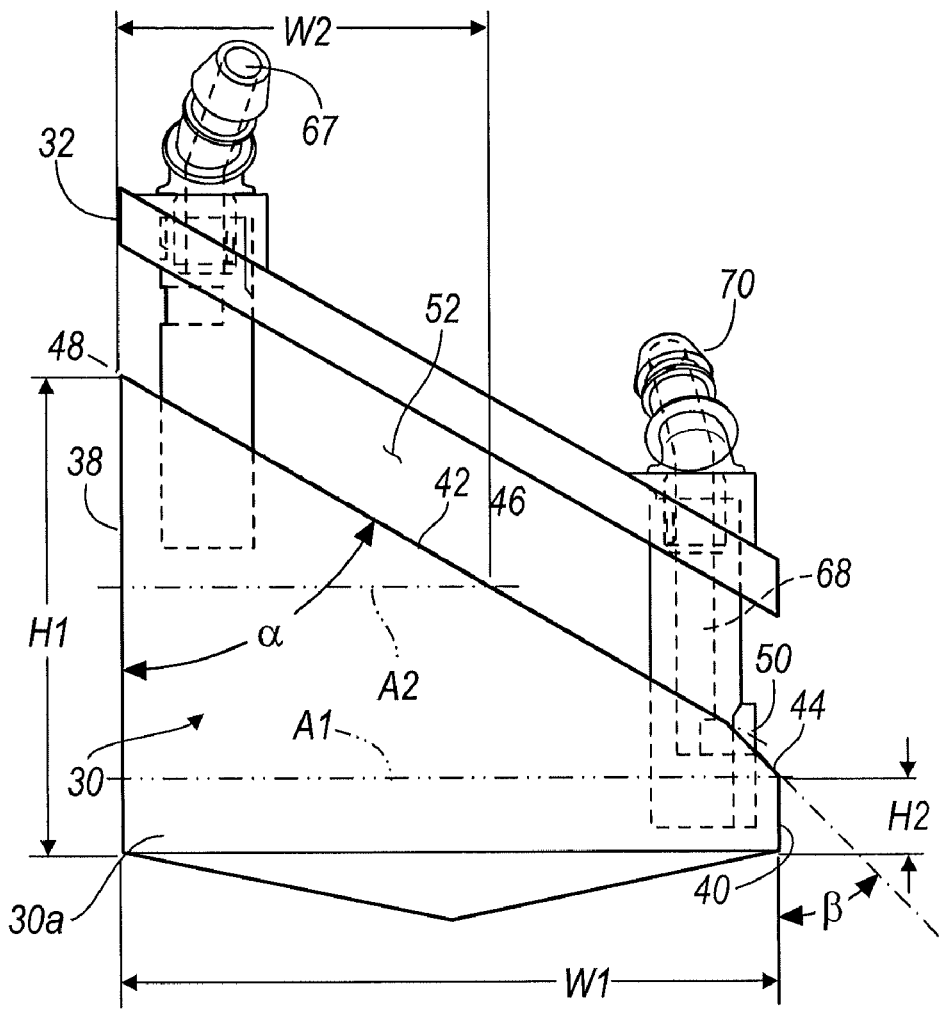
FIG. 9A
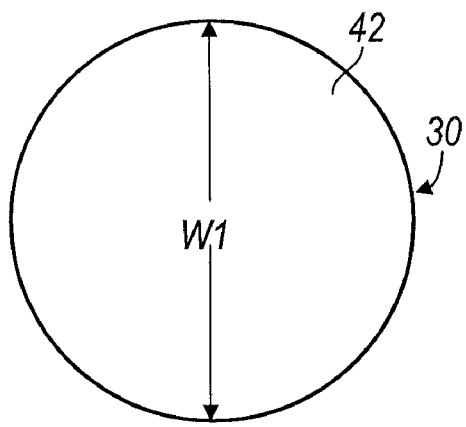
FIG. 9A1
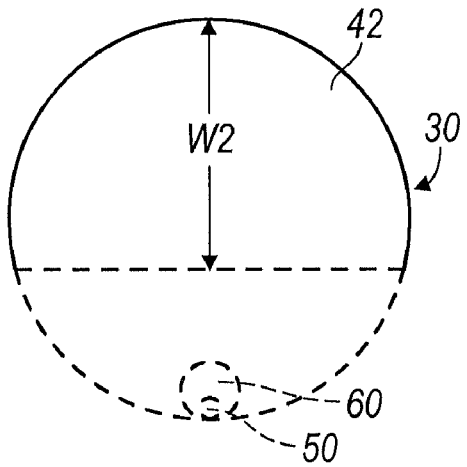
FIG. 9A2

BUOY SUSPENSION FRACTIONATION SYSTEM

CROSS-REFERENCE TO RELATED APPLICATIONS

This application includes subject matter similar to concurrently filed U.S. patent application Ser. No. 12/101,594, filed on Apr. 11, 2008, now U.S. Pat. No. 7,806,276, issued on Oct. 5, 2010, incorporated herein by reference.

This application claims the benefit of U.S. Provisional Application No. 60/911,407, filed on Apr. 12, 2007. The disclosure of the above application is incorporated herein by reference.

FIELD

The present teachings relate to a separator that uses density differences to fractionate a suspension such as blood.

BACKGROUND

Clinicians have identified a wide range of therapeutic and laboratory applications for autologous isolated fractions, such as platelet concentrate, platelet-poor-plasma, and stromal cells, of suspensions such as blood, bone marrow aspirate, and adipose tissue. Clinicians generally prefer to draw and fractionate the autologous suspension at the point-of-care. Point-of-care fractionation can reduce the need for multiple appointments to draw and fractionate the autologous suspension which can be costly and inconvenient. Additionally, point-of-care preparation reduces potential degradation of the autologous suspension that can begin once the autologous suspension is removed from a patient. Point-of-care fractionation systems should be easy to operate to reduce the need to provide clinicians with extensive instruction, quick so the therapeutic fraction can be isolated and administered during a single patient visit, efficient to effectively isolate the fraction to a desired concentration, and reproducible to operate over wide variations in suspension characteristics. An example of a buoy based suspension fractionation system is shown in Biomet Biologics, Inc. international brochure entitled "*Gravitational Platelet Separation System Accelerating the Body's Natural Healing Process.*" 2006

SUMMARY

A buoy suspension fractionation system comprises a separation container and a buoy. The separation container defines a volume enclosed by a container wall, a container bottom, a container top and an access port to access the volume. The buoy is carried in the separation container and has a tuned density that is configured to reach an equilibrium position in a suspension. The buoy comprises a buoy upper surface and a buoy sidewall defining a height, a transverse dimension, and a perimeter. The buoy further comprises a guide surface and a collection space above the buoy upper surface. The guide surface is carried on the buoy upper surface and is inclined to an accumulation position near the buoy perimeter. The buoy suspension fractionation system can be used in a method of isolating a fraction from a suspension, and in a method for isolating a fraction and re-suspending isolated particulates for withdrawal.

BRIEF DESCRIPTION OF THE DRAWINGS

The present teachings will become more fully understood from the detailed description and the accompanying drawings, wherein:

FIG. 9A is a plan view of a buoy according to various embodiments;

FIG. 9A1 is a plan view of a buoy at a selected transverse plane;

FIG. 9A2 is a plan view of a buoy at a selected transverse plane;

DETAILED DESCRIPTION OF VARIOUS EMBODIMENTS

Figure 1:
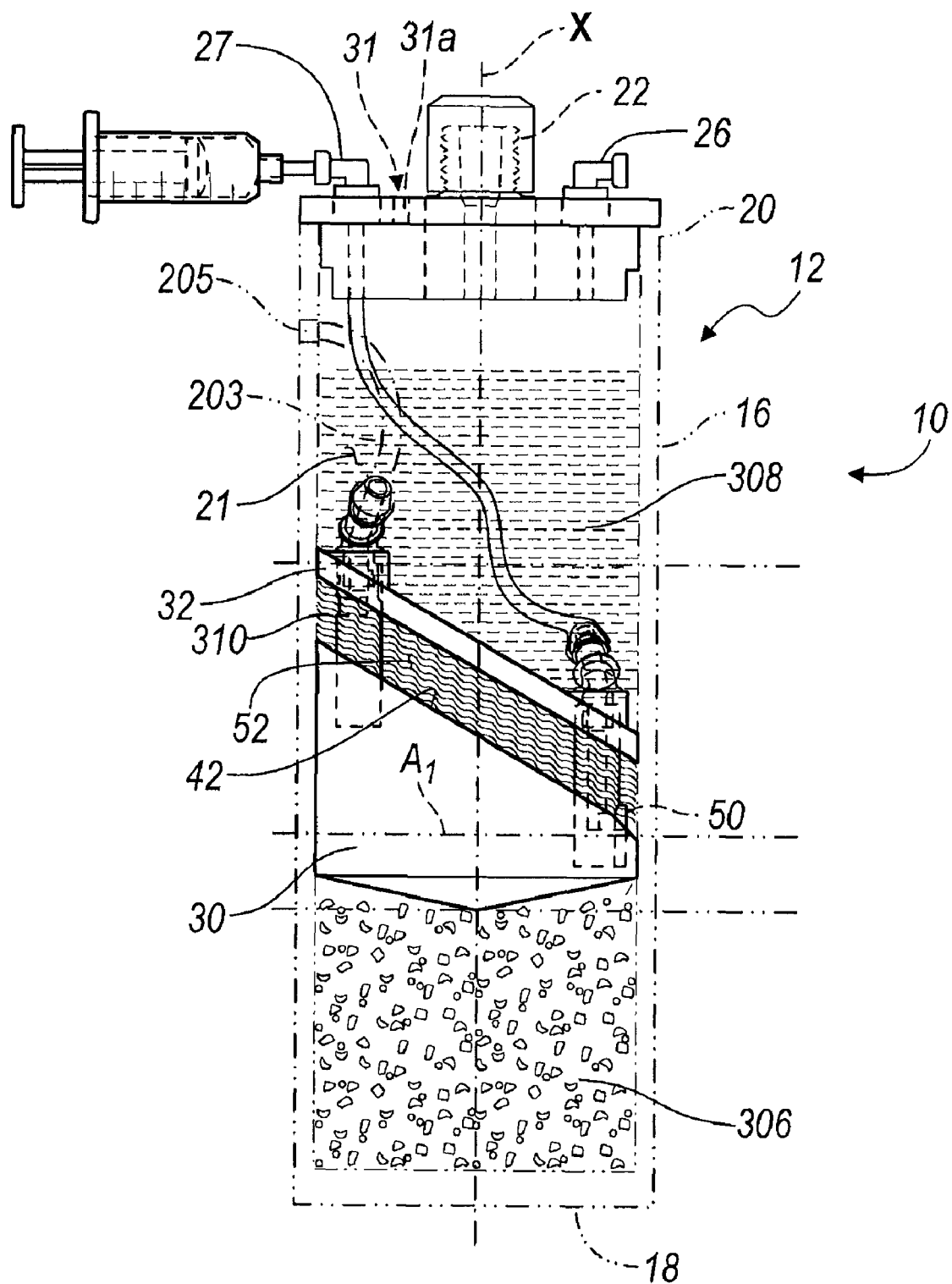
FIG. 1 is an environmental view of a fractionation device including a suspension fractionated during the centrifuge process.

FIG. 1 shows a buoy suspension fractionation system 10, according to various embodiments that can be used in a clinical or laboratory environment to isolate fractions from a suspension or multi-component material removed from a patient or a preparation of extracted or excised material from a patient. The suspension can include a sample of blood, bone marrow aspirate, cerebrospinal fluid, adipose tissue, and the isolated fractions can include platelets, platelet poor plasma, platelet rich plasma and stromal cells. The isolated fractions can each have equilibrium point or positions within the separation container that are achieved when separation has occurred. For example, a buffy coat of whole blood may have an equilibrium position above that of the red blood cells when a sample of whole blood is separated.

Isolated fractions can be used in a variety of clinical applications, animal applications, and laboratory applications. Some of the clinical applications include peripheral vascular disease, orthopedic surgery, plastic surgery, oral surgery, cardio-thoracic surgery, brain and neural procedures, and wound healing. Laboratory applications include isolating, creating or synthesizing therapeutic materials or materials for analysis from fractions produced by the fractionation system.

Although the fractionation system 10 can be used allogeneically, such as with pooled blood, the fractionation system 10 can be used autologously to reduce risks of potential incompatibility and contamination with pathogenic diseases. Also, other autologous materials can be used including cerebrospinal fluid, cerebrospinal fluid can be obtained via a spinal tap or other appropriate collection procedure. A general description of a fractionation system is provided in a Biomet Biologics, Inc. international brochure "*Gravitation Platelet Separation System Accelerating the Body's Natural Healing Process*" (2006) and a description of a therapeutic procedure using platelet concentrate is shown in a Biomet Biologics, Inc. international brochure "*Shoulder Recovery with the GPSO® Platelet Concentration System*" (2004), incorporated herein by reference.

Figure 7:
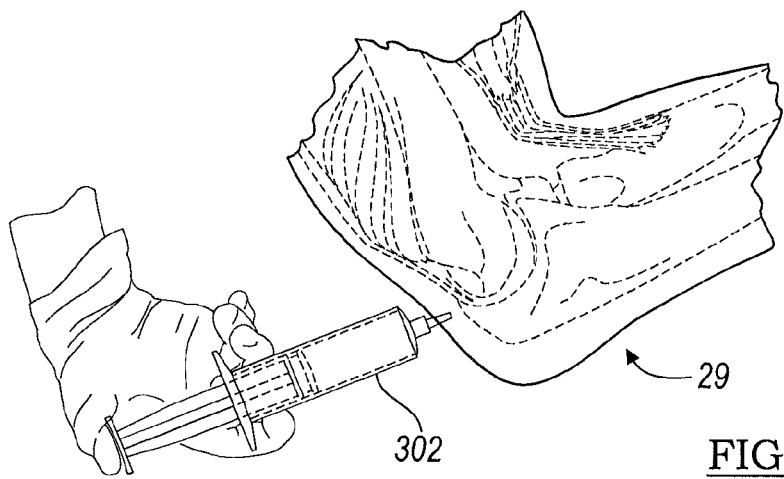
FIG. 7 is an environmental view of a therapeutic application of the second fraction.

FIGS. 2-7 show exemplary fractionation system operational steps for a clinical therapeutic application embodiment. The operational steps begin in FIG. 2 by inputting autologous (although pooled blood can be used) whole blood into the fractionation system 10, via an access port 22. The fractionation system 10 is placed into a centrifuge 23 in FIG. 3 and spun about five minutes to about twenty minutes at a rate of about 320 rpm to about 5000 rpm (this speed may produce a selected gravity that may be approximately 7.17×g to about 1750×g (times greater than the normal force of gravity)). The first fraction or top fraction 308 (FIG. 1), which can be platelet-poor-plasma according to various embodiments including from a whole blood sample, is shown being removed in FIG. 4. The fractionation system 10 is agitated in FIG. 5 to re-suspend at least a portion of a second fraction 310, which can be platelet-rich-plasma or platelet concentrate, according to various embodiments including from whole blood fractionation. The second fraction is removed from the fractionation system 10 in FIG. 6. Finally, the second fraction is applied as part of a therapy, such as shown in FIG. 7 to treat elbow tendonitis. The second fraction can be injected into a selected portion of an elbow 29 to treat tendonitis.

It will be understood that the buoy 30 can be altered depending upon the material placed in the container 12. For example, if neural stem cells are to be separated from cerebrospinal fluid then the buoy 30 can have a density to allow collection of the neural stem cells in the collection area 52 of the system 12. The collected neural stem cells can also be applied for therapeutic reasons or used in laboratory study, isolation, culture, etc.

Figure 8:
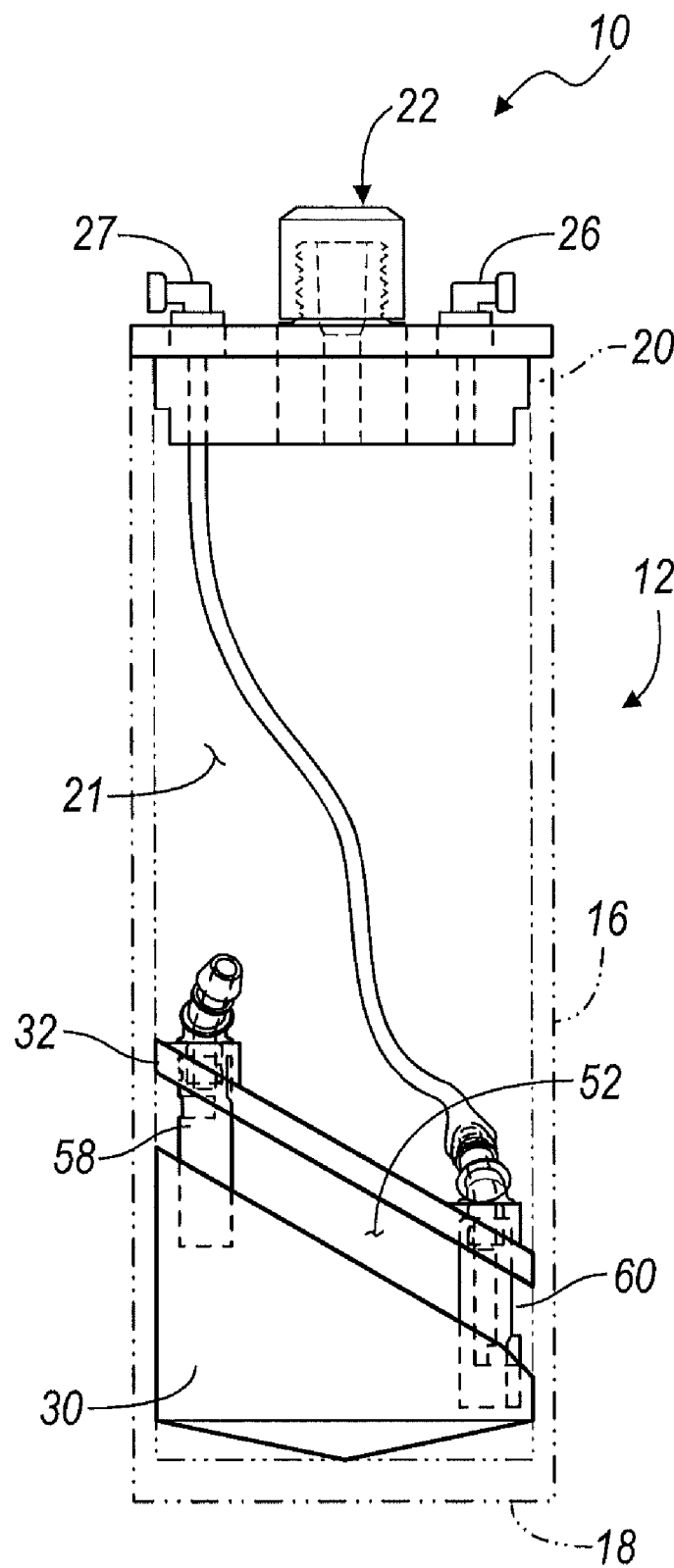
FIG. 8 is an environmental view of a separation container and a buoy.
Figure 9B:
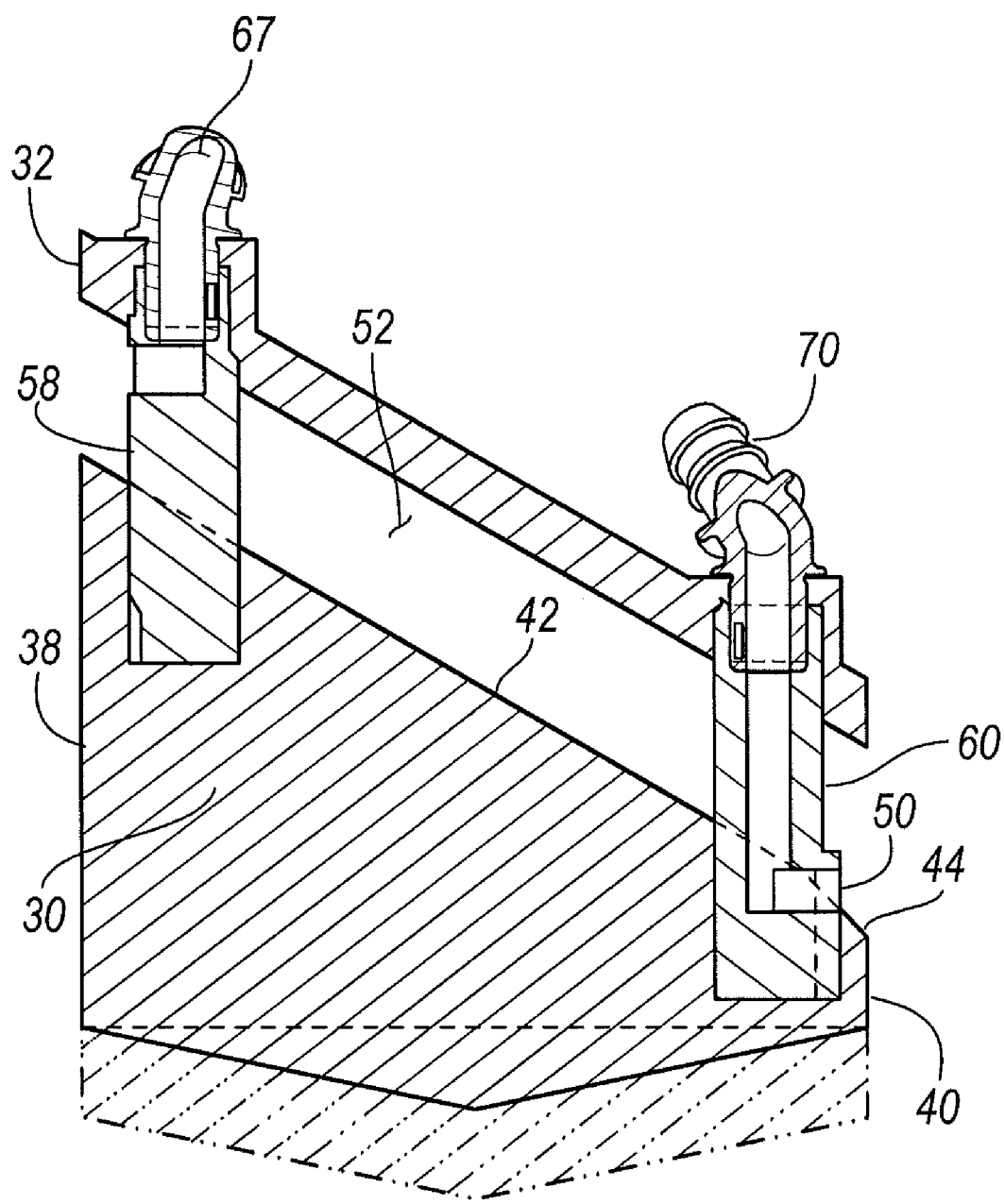
FIG. 9B is a cross-sectional view of the buoy of FIG. 2A.

Returning reference to FIG. 1 and with additional reference to FIGS. 8-9B, the suspension fractionation system 10 comprises a separation container 12 and a buoy 30. The separation container 12 can be a separation tube having a container wall 16, a container bottom 18, and a container top 20 enclosing a volume 21 that can be accessed by one or more access ports 22, 26, 27, and a container vent 31. The container 12 may be formed of any appropriate material, such as the Cryolite Med® 2 material sold by Cyro Industries Evonik Degussa Corp. The container 12 can be about 50 mm to about 150 mm in height, including about 102 mm in height. The container 12 can have an internal diameter of about 20 mm to about 40 mm, including about 25 mm to about 35 mm and define a volume of about 30 ml to about 100 ml, including about 30 ml to about 60 ml. The separation container 12 can have any appropriate shape, such as an oval, provided the buoy 30 is shaped to conform to the separation container 12. Though not particularly illustrated, the separation container 12 can also have more than one compartment, such as a separation tube and an area to transfer tube contents away from the separation tube 12. For example, a separate compartment can be formed to house the assembly of the buoy 30 and isolator 32 separate from another area.

The various ports 22, 26 and 27 can be provided to allow access to any appropriate compartment of the container 12. The access ports 22, 26, 27 can be any means that allow communication from outside the separation container 12 to the separation container volume 21 such as a Luer lock port, a septum, a valve, or other opening. The container vent 31 allows movement of air between the inside and outside the separation container 12 to equalize pressure when suspension in introduced into or withdrawn from the separation container 12. The container vent 31 can include a vent filter 31a to serve as a sterile barrier to allow air to enter the separation container 12 while preventing undesired materials from entering the separation container 12.

When the separation container 12 is at rest, a buoy perimeter 30a and the container wall 16 can be dimensioned to form an interference fit to hold the buoy 30 at a position in the separation container 12. When the separation container 12 is centrifuged, the buoy perimeter 30a and the container wall 16 have clearance allowing the buoy 30 to move within the separation container 12 and a material to pass between the buoy perimeter 30a and the container wall 16. For example, the container 12 can compress axially to increase its internal diameter. Alternatively, the buoy 30 could have an opening (e.g. FIG. 16), such as a centrally or internally located opening 176 or a peripheral channel 168a (FIG. 13) running the height of the buoy, which would allow a material to move through the buoy.

The buoy 30 is carried in the separation container 12 and has a tuned density that is configured to reach a selected equilibrium position in a suspension. The buoy can have its density tuned in the range from about 1.0 g/cc to about 1.10 g/cc, such as about 1.06 g/cc. The buoy 30, according to various embodiments, can be formed to include the tuned density and can be formed of one or more materials to achieve the tuned density.

For example, the density of about 1.06 g/cc can position the buoy 30, or a selected part of the buoy 30 including the collection area 52, at an equilibrium position of a buffy coat of a separated whole blood sample. In a further example, the density can also be tuned so that the collection area 52 is near an equilibrium position, such as where neural stem cells collect in a selected suspension. Regardless of the density of the buoy 30, it can be selected to position the buoy 30 at an equilibrium position of a selected material.

As illustrated in FIG. 1, the collection area 52 is positioned within the container 12 after a separation procedure has occurred. The collection area, defined relative to the buoy 30, is positioned at the equilibrium position of the separated or isolated fraction 310 in the container. The equilibrium position of a selected fraction can be defined as its position within the container relative to other fractions in the container of a separated sample or material. The equilibrium position can also be defined relative to the axis X of the buoy 30 or the container 12. The equilibrium position, however, may depend upon the amount of the sample of the amount of a selected fraction within a sample. According to the illustration in FIG. 1, the equilibrium position of the fraction 308 is above or nearer the top 20 of the container 12 than the equilibrium position of the fraction 310. Thus, the buoy 30 can be tuned, such as including a selected density or specific gravity, to position the collection area 52 relative to an equilibrium position of any selected fraction.

The buoy comprises a buoy upper surface 48 and a buoy sidewall 38, 40 defining a height H1, H2, a transverse dimension at planes $A_1$, $A_2$, and a perimeter 30a, discussed further herein. The buoy further comprises a guide surface 42. In some embodiments, the buoy can further comprise a collection port 50 and a precision collection region 44. The collection port 50 communicates with the access port 27 and communicates with a collection space 52 above the buoy upper surface 42 and can be located near the buoy perimeter 30a. In some embodiments, the collection port 50 is not carried on the buoy, but rather the collection port is a withdraw device such as a syringe that is inserted through an access port or top of the tube 12.

With reference to FIG. 9A, the buoy 30 has a first height dimension H1, a second height dimension H2, a maximum width or transverse cross sectional area W1 at plane A1, a second width or transverse cross sectional area W2 at plane A2, a guide surface angle $\alpha$, and precision collection area 44 including a surface 46 defining a precision collection region angle $\beta$. The height of the buoy 30, according to various embodiments, can be defined relative to a central axis X, which can also be a longitudinal axis X of the container 12. The sidewalls of the buoy 30 and the container 12 can also be substantially parallel to the axis X. Although certain dimensions are shown in FIG. 9A, the buoy perimeter could be shaped differently provided the perimeter conforms to the separation container 12.

The guide surface 42 is carried on and/or defined by the buoy upper surface 48 and is inclined to an accumulation position at or near the buoy perimeter. The guide surface 42 serves as a guide means for conveying particles down an incline toward an equilibrium interface or collection region. The guide surface 42 can be inclined relative to the buoy sidewall 38 height for a distance of more than one-half the buoy transverse dimension or width W1, such as about two-thirds the buoy transverse dimension, and in various embodiments the guide surface can be inclined relative to the buoy sidewall 38 substantially throughout a length of the guide surface 42.

Figure 10:
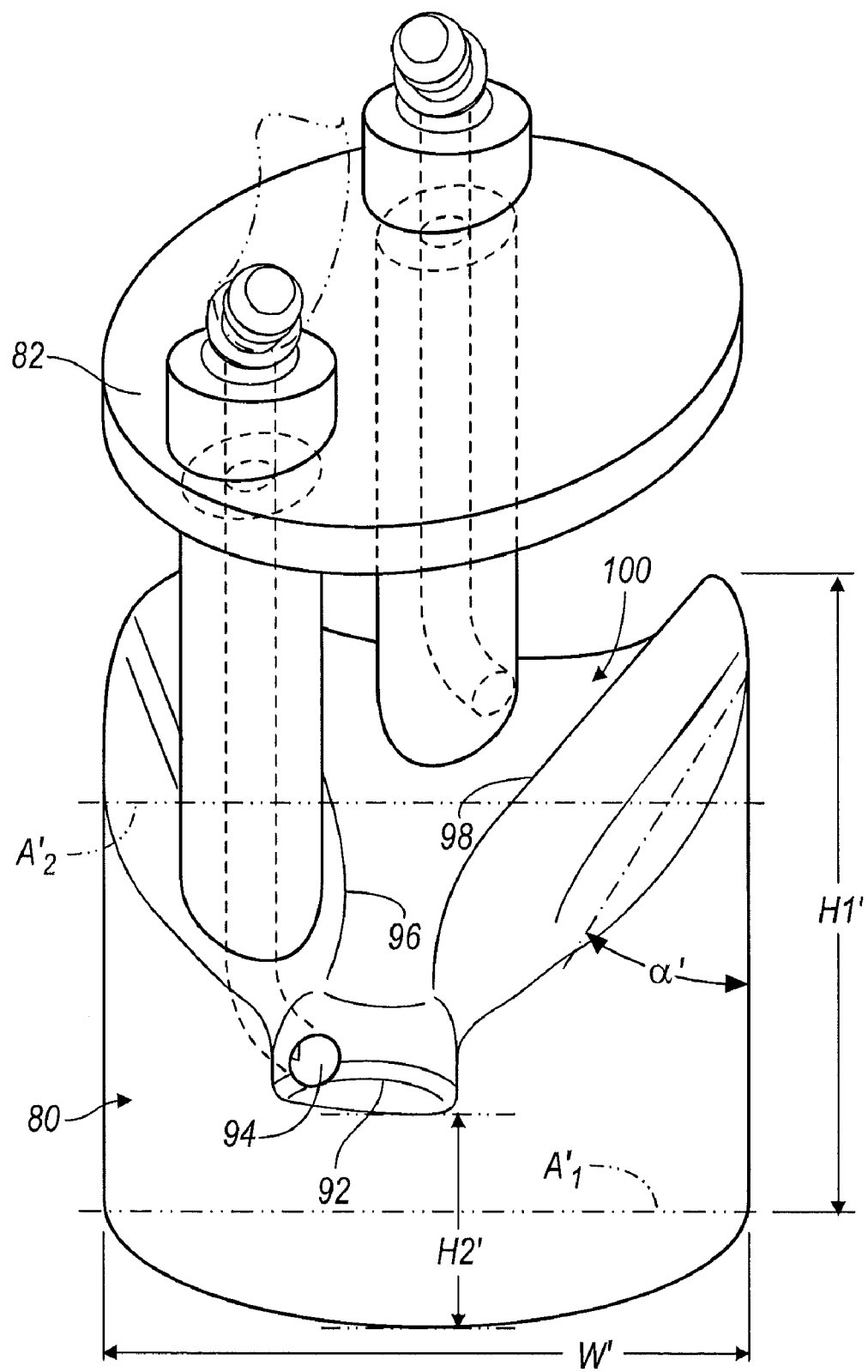
FIG. 10 is a perspective view of a buoy, according to various embodiments.
Figure 12:
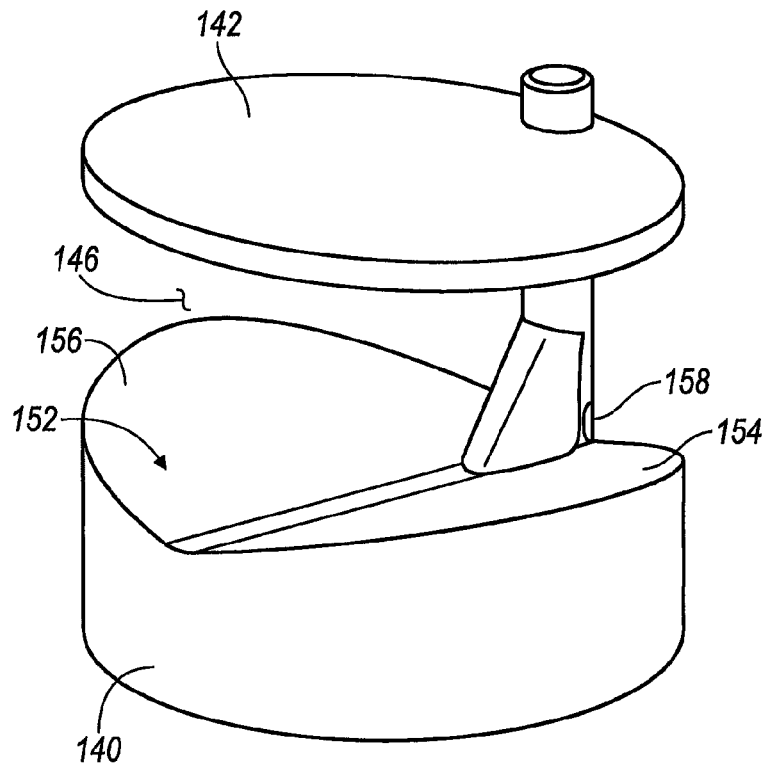
FIG. 12 is a perspective view of a buoy, according to various embodiments.

The guide surface 42 can be substantially planar and can have an average angle in the range from the minimum for particulates to move down the guide surface, regarding blood platelets, for example, about 10 degrees to about 60 degrees. For example, angle $\alpha$ can be about 5 degrees to about 89 degrees, or greater, including about 30 degrees to about 89 degrees. Angle $\alpha$ can, exemplary, be exactly or about 60 degrees in various embodiments. In some embodiments, the guide surface can include contours defined in the guide surface with multiple angles such as shown in FIGS. 10 and 12. For example, in FIG. 10, a buoy 80, according to various embodiments, can include two guide surface contour walls 96, 98 to assist in defining a guide surface 100. The two walls 96, 98 can define a trough that extends a selected distance across the guide surface 100, such as more than two thirds. The trough can define an area of the guide surface that is lower than the surrounding area. A contoured precision collection region 92 can also be defined that communicates with a port 94. In FIG. 12, a buoy 140 can include a guide surface 152 that includes two inclined sides 154, 156 angled towards a selected region, such as a center of the guide surface 152. The entire guide surface can also be inclined towards a collection port 158, in an amount as discussed above.

Figure 2:
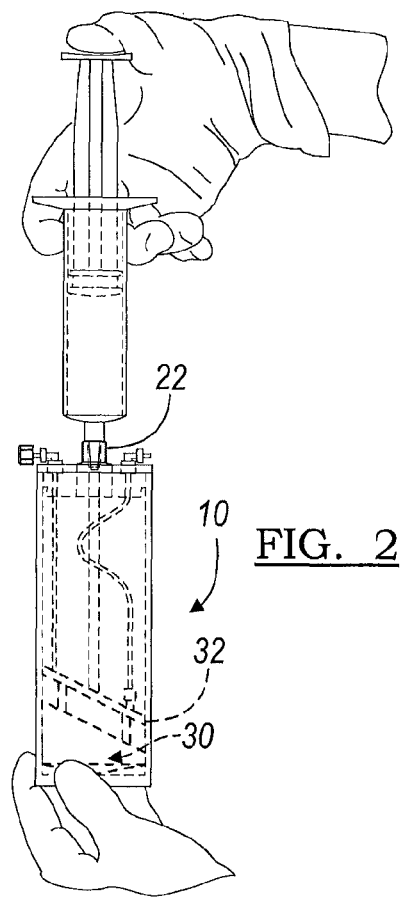
FIG. 2 is an environmental view of a suspension being added to a fractionation device.
Figure 3:
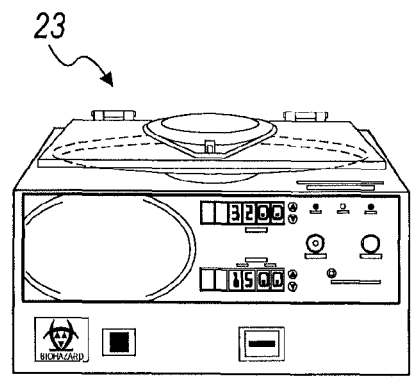
FIG. 3 is an environmental view of a centrifuge.
Figure 4:
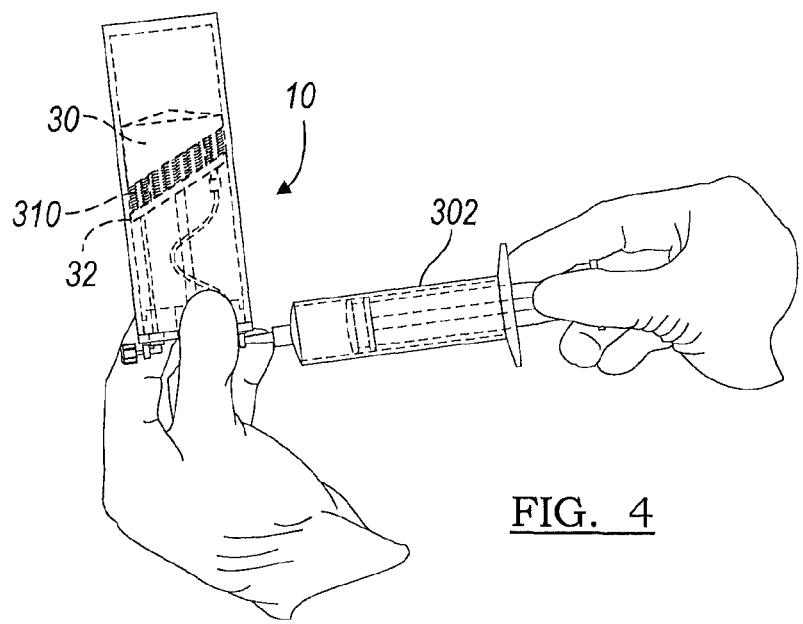
FIG. 4 is an environmental view of a first fraction being removed from the fractionation device.
Figure 5:
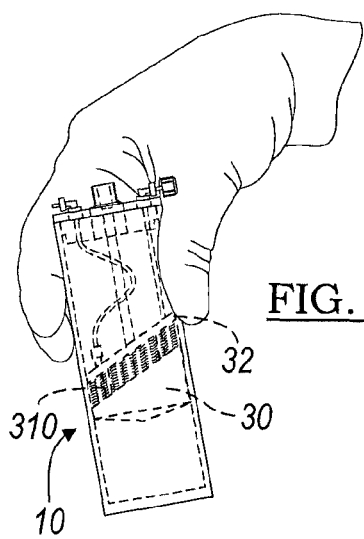
FIG. 5. is an environmental view of the fractionation device being agitated to re-suspend a portion in a second fraction.
Figure 6:
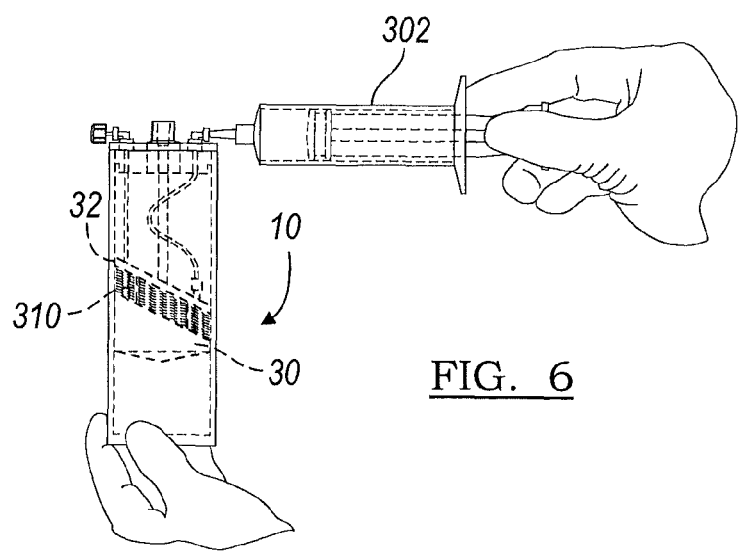
FIG. 6 is an environmental view of the second fraction being removed from the fractionation device.

In various embodiments, as exemplary illustrated in FIGS. 9A, 9A1, and 9A2 the different buoy transverse cross-sectional areas W1, W2 can be defined at various planes, such as $A_1$, $A_2$, etc. As illustrated, various transverse cross-sectional areas can be defined by the buoy 30 due to the angled top wall 42. The transverse cross-sectional areas defined at the various planes $A_1$, $A_2$ can be positioned at selected locations based upon characteristics of the buoy 30, such as density. The height H2, angle $\alpha$, etc. The width dimension can be 1 inch to about 2 inches including about 1.347 inches (about 25 mm to about 51 mm, including about 34.21 mm) for W2. The dimension of W1 can depend upon the selected location of plane A1. These dimensions can achieve various areas depending upon the geometry of the buoy 30. Nevertheless, the area at plane A2 can be substantially similar to an area at a transverse plane within the container 12.

In use, the substantially maximum transverse cross-sectional area W1 of the buoy 30 can be positioned at a selected location. As illustrated in FIG. 9A1, the maximum cross-sectional area is at plane $A_1$. The plane $A_1$ can be positioned at or near a selected equilibrium interface, in use. The position of the plane $A_1$ is selected by selecting a density of the buoy 30 and the known or estimated density of the material into which the buoy 30 is positioned. The buoy's maximum transverse cross-sectional area near the intended or selected interface results in a substantially maximum change in displacement of the relative volume of a fraction below the equilibrium interface and substantially maximum change in displacement of a fraction above the equilibrium interface relative to change in the axial orientation of the buoy relative to the interface. This can improve fractionation isolation by ensuring that the maximum transverse cross-section displaces a maximum amount of area within the container 12 at the selected interface. For example, more than 90% of a whole blood's platelets can be isolated.

Thus, in applications involving suspensions, such as whole blood, which may be variable in composition between samples, sample density variation will result in minimal variation in the axial orientation of the buoy relative to a selected equilibrium interface. The minimal variation in axial location of the buoy 30 in the container 12 is based at least in part on the maximum displacement of a material in the container at the maximum transverse cross-section of the buoy 30. In other words, for each small variation of axial location of the buoy 30, a maximum displacement occurs. In selected uses, the buoy's maximum cross-sectional plane $A_1$ is provided at a selected location and the minimal axial variation helps to ensure the plane $A_1$ is properly placed.

Additionally, at or near the buoy's maximum transverse cross-sectional area, the cross-sectional area of the fractionated material is near minimal. Simply, within the container 12 at a selected position if a maximum transverse cross-section of the buoy 30 is at a selected position, then a relatively minimal amount of other material can be present at the same location. In combination, the minimization of cross-sectional area of fractionated material and minimization of variation of axial orientation of the buoy in relation to an equilibrium interface results in minimization of variability of fractionated material volume near the interface.

The precision collection region 44, 92 (FIGS. 9A, 9B, and 10) can be interposed between the guide surface and the accumulation position at or near the buoy perimeter. The precision collection region 44, 92 serves as a precision collection structure for collecting a precise, high yield and/or pure amount of a selected fraction. The precision collection region 44, 92 can be raised or lowered in relation to the buoy perimeter to vary the fraction in the collection region without the need to make substantial changes to other buoy design features. In other words, the dimension H1 can be changed. Generally, the height H2 can be about 2.5 mm to about 5.1 mm. The height H1 will generally be constrained by the height H2 and the angle α. According to various embodiments, the precision collection region 44 is shown in FIG. 9A formed at an angle β in relation to the sidewall 40. The angle β can be any appropriate angle such as about 10 degrees to about 60 degrees, including about 45 degrees. According to various embodiments, the precisions collection region 92 can be contoured, FIG. 10.

According to various embodiments, an isolator 32, is coupled to the buoy 30. The combination of the isolator and buoy, according to various embodiments, can also be referred to as a separation assembly member. Exemplary isolators 82, 122, 170, 180, 190 are illustrated coupled to exemplary buoys 80, 120, 140, 160, 182, 192. The isolator 32, for example, provides a means for creating the collection compartment 52 and comprises one or more spacers 58, 60 to position the isolator 32 apart from the buoy 30 to create the collection compartment 52. A withdraw port 70 can be carried on the isolator 32 communicating with the withdraw port 27 and the collection port 50. The spacer 58, 60 can also serve as a conduit 68 between the collection port 50 and a withdraw or withdraw port 27. The withdraw port 27 serves as a structure for withdrawing the isolated or second fraction 310 from the collection compartment 52.

The isolator 32 can be configured from a material with a lower density than the buoy 30, such as a density of about 1.0 g/cc or less. A volume of the isolator 32 can be substantially less than a volume of the buoy 30. The isolator 32 can be configured so the isolator volume and the buoy volume combined below a selected equilibrium interface are greater than the isolator volume and the buoy volume combined above the equilibrium interface. As discussed above, an equilibrium interface can include a position relative to the platelet concentrate or buffy coat from a centrifuged whole blood sample, such as at or just below the platelet concentrate or buffy coat. By configuring the isolator 32 and buoy 30 with more volume below the equilibrium interface than above the equilibrium interface, the buoy 30 operates in a more repeatable manner even between a wide range in variations in compositions such as whole blood where the variability in density of a more dense fraction (e.g. red blood cells) is less than the variability in density of a less dense fraction (e.g. plasma). For example, the make up of a whole blood sample from one patient to the next can be markedly different.

Between individual patients, the density of the red blood cell or erythrocyte fraction of a whole blood sample can generally vary less than the density of a plasma or serum portion of a whole blood sample. Therefore, positioning a greater volume of the isolator and buoy within the denser fraction can assist in having highly repeatable and highly efficient collection or separation of a whole blood sample. The height H2 can be varied or selected to ensure a maximum or selected volume of the isolator and buoy are positioned within the denser fraction of the whole blood sample.

Figure 11A:
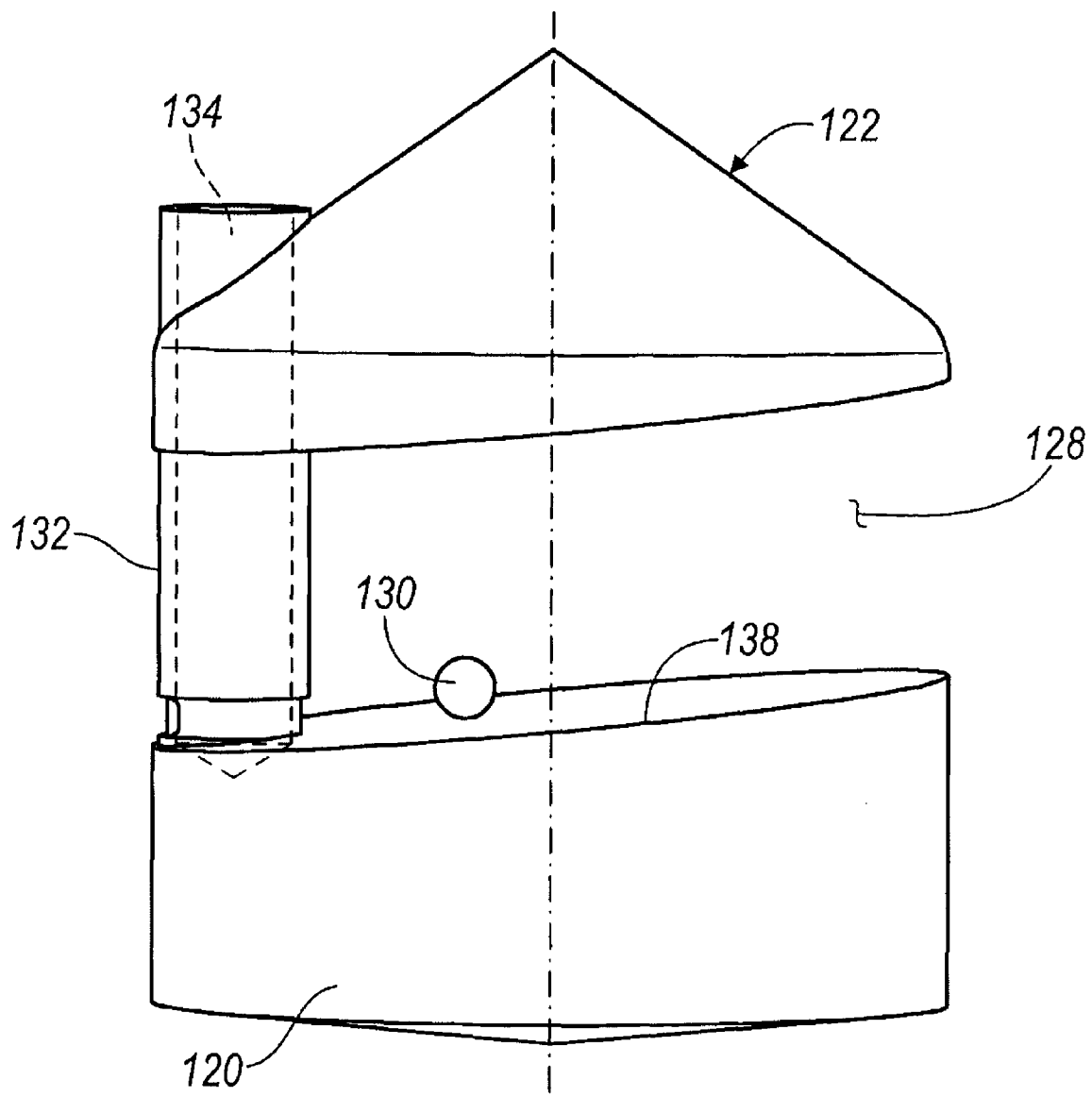
FIG. 11A is a perspective view of a buoy, according to various embodiments.
Figure 11B:
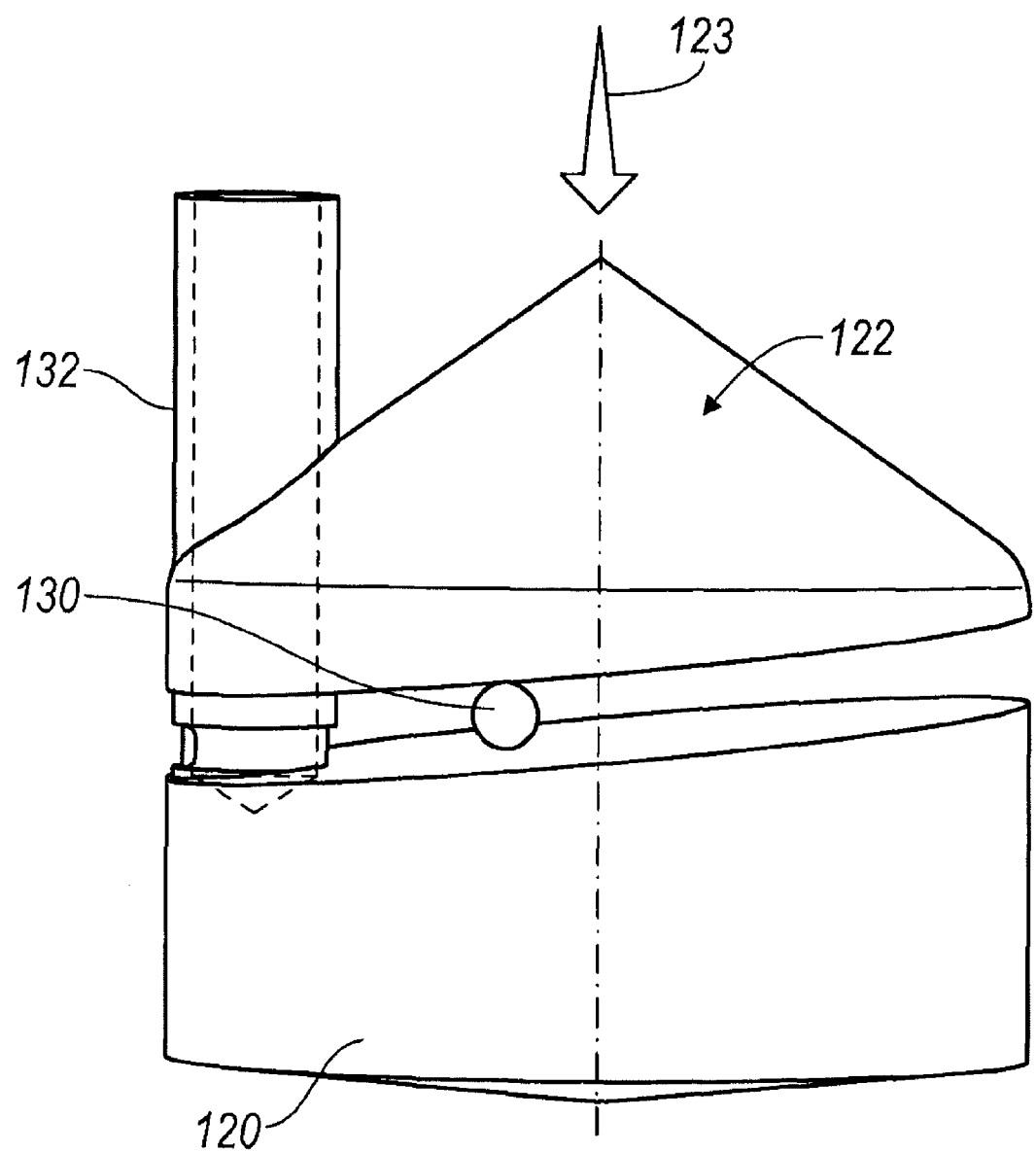
FIG. 11B is a perspective view of a buoy in a closed position, according to various embodiments.

According to various embodiments, the isolator may include various features. An isolator 122 can be configured to move relative to a buoy 120, as illustrated in FIGS. 11A and 11B. The isolator 122 can move along a column or spacer 132 in the direction of arrow 123 during extraction of a selected fraction. The isolator 32, 82 can also be substantially uniformly thick or vary in thickness 122, 180, 190.

Figure 13:
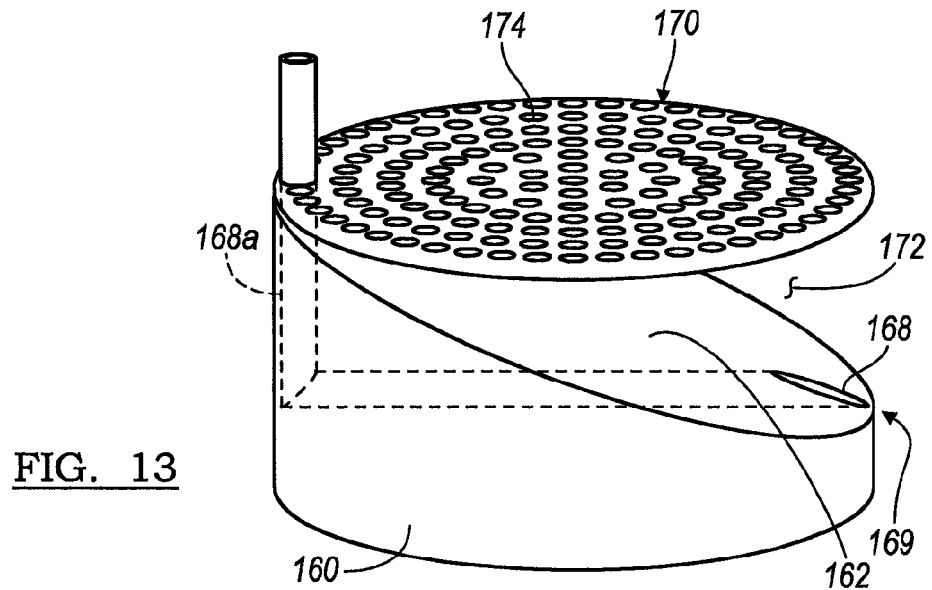
FIG. 13 is a perspective view of a buoy, according to various embodiments.

An isolator 170 can include collection openings 174 (FIG. 13). The isolator 32 can also include a collection vent 67 (FIG. 9A), which can also include a collection valve, a collection passage, or a collection vent tube or passage 203. The collection openings 174 can reduce the distance particles, such as platelets which are fragile and adherent, travel to reach a guide surface 162 and reduce the time that particles are in contact with surfaces. Various types of collection openings can be used.

The collection openings 174 can be sized to permit selected particles to pass yet sufficiently small so suspension fluid tension maintains adequate isolation of the collection compartment. The collection openings can also include various valves such as a duck bill or flapper bill which can open under certain conditions and close under others. A collection valve can be interconnected with any appropriate portion such as with a collection port 70 or passage 68.

The collection vent passage 67 through the isolator 32 equalizes pressure when fluid is withdrawn from the collection area 52. The spacer 58 can serve as a conduit for the collection vent passage 67, the collection port 50, or both. The collection valve communicates with the collection vent passage 67 to control collection vent passage 67 operation and close the collection vent passage 67 during re-suspension agitation. The collection vent tube 203 communicates with the collection vent passage 67 and air. The air can be the air above the collection area 52 (i.e. a portion of the suspension above the isolator 32 has been removed) or through an opening 205 in the container wall and generally through a sterile barrier (e.g. a sterile foam filter). The collection vent tube 203 allows removal of fractionated suspension in the collection compartment without the need to remove the fraction, such as plasma, above the isolator 32. Although, without a collection vent tube 203, the fraction above the isolator could be removed and the collection area could be vented to the area above the isolator.

Various embodiments further comprise a mechanical agitator 130 carried in a collection compartment 128 (for example FIGS. 11A and 11B).

The isolator 122 is moveable relative to the buoy 120. The isolator 122 can be in an open position after centrifugation of the separation container. During removal of material from the collection compartment through the collection port 134, the isolator 122 can move in the direction indicated by arrow 123 toward the buoy 120 to decrease or close the volume of the collection compartment 128.

The buoy 30 can also be formed in a plurality of selectable sizes, having different dimensions, such as those illustrated in FIG. 9A. The axial dimensions of the buoy 30 can be selected to achieve an appropriate displacement of the suspension in the container 12, especially after fractionation has occurred. Angle α, defined between the outer edge 38 and the surface 42 can be any selected angle. For example, angle α can be about 30 degrees to about 89 degrees, including about 60 degrees. The angle α can generally be created to be as small as possible to allow a steep angle of the surface 42 towards the inlet port 50 that will not damage the material being collected within the collection space 52. As discussed above, the height H2 can be selected to determine or select the amount of the buoy 30 positioned within a selected fraction, such as a dense fraction, of a sample separated within the separation system. Height H2 can be about 0.1 inches to about 0.2 inches, including about 0.18 inches (about 2.5 mm to about 5.1 mm, including about 4.57 mm). An exemplary height H2 is 0.1795 inches (4.559 mm), depending upon selected applications, the size of the separation system, and other selected factors. Nevertheless, the height H1 is generally defined by the height H2 and the angle α. Height H1 can be about 0.8 inches to about 1.2 inches, including about 1 inch (about 20 mm to about 30 mm, including about 25 mm). An exemplary height H1 can include 1.0 inches (25 mm). The positioning of the collection area 52, including the inlet port 50, can be based upon the height H2 and how the buoy 30 interacts with the material into which it is positioned, via the height H2.

Figure 17:
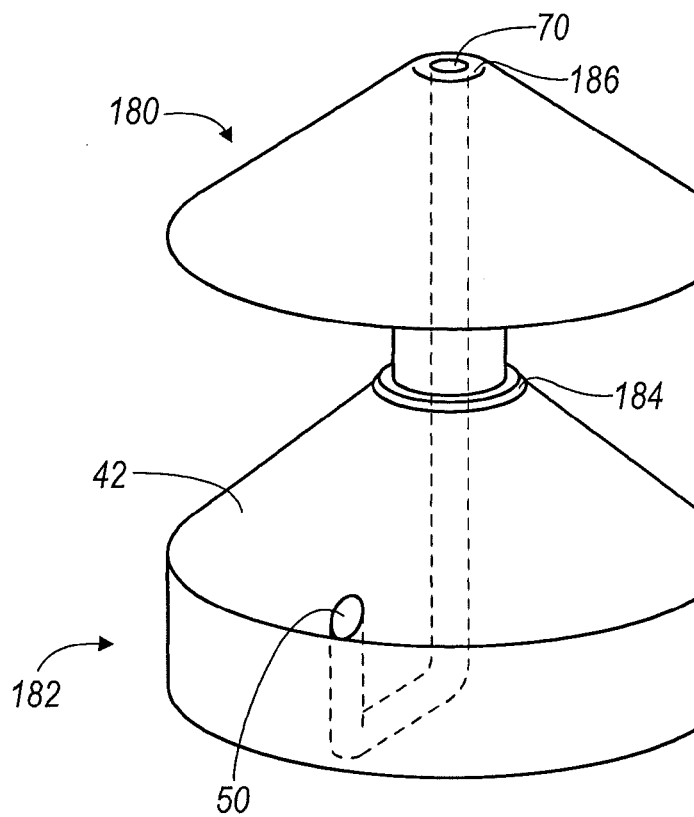
FIG. 17 is a plan view of a buoy, according to various embodiments.

A buoy 182, as illustrated in FIG. 17, can include an isolator 180 positioned relative thereto. The isolator 180 can include a center placed substantially over a center of the buoy 182. The center of the buoy 182 and the isolator 182 can both be defined by peaks or apexes 184 and 186, respectively.

Figure 18:
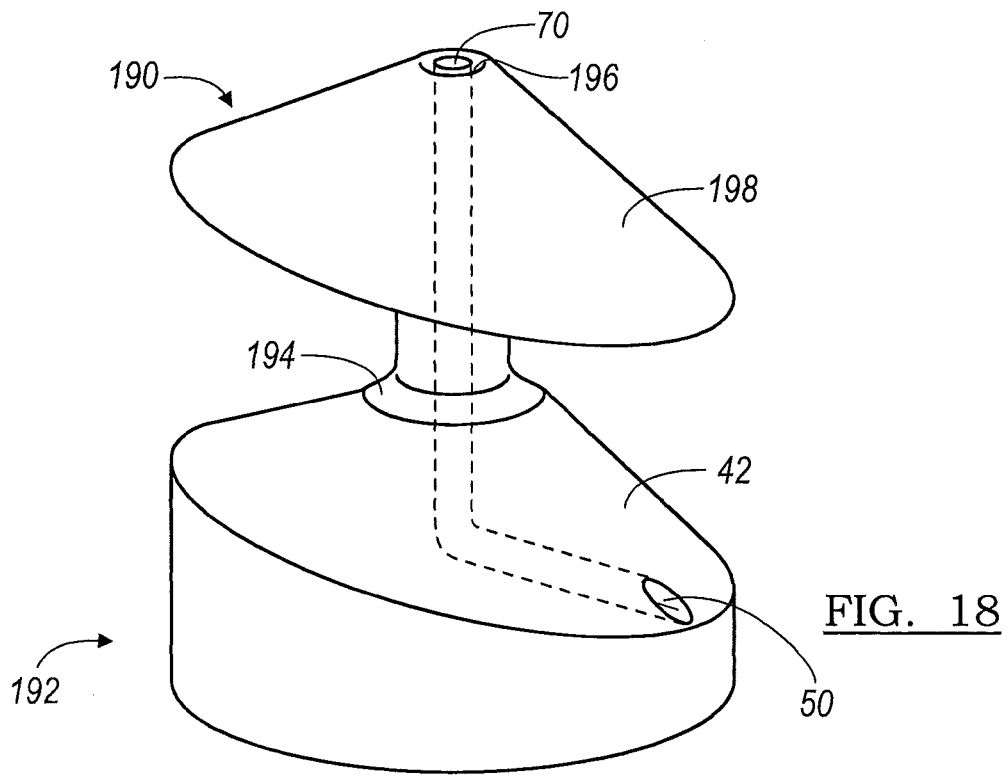
FIG. 18 is a plan view of a buoy, according to various embodiments.

A buoy 192, as illustrated in FIG. 18, can also be positioned relative to an isolator 190. The buoy 192 can include an apex 194 near a center of the buoy 192 and the guide surface extending from an edge of the buoy 192 to a second edge of the buoy 192. The isolator 190 can also include an apex 196 generally near its center. The isolator 190 can also include a surface 198 that extends from one edge of the isolator to another edge of the isolator 190.

The isolators 180, 190 can act substantially similar to the isolator 32, discussed above. The isolator 180, 190 can define an angle between an apex or the withdrawal port 70 and an outer edge of the isolators 180, 190. The upper surface of the isolators can include an angle to assist in directing a selected material, such as a platelet fraction of whole blood sample, to the collection area or surface 42 of the buoys 182, 192. Generally, the isolators 180, 190 can include a height or volume to substantially minimize the volume of the isolator 180, 190 relative to the buoys 182, 192. As discussed above, this can assist in positioning the buoys 182, 192 relative to a dense (e.g. red blood cell) fraction of a whole blood sample. The angle of the isolators 180, 190 and the height of the isolators 180, 190 can be selected to provide for a minimal distance of travel or least disturbance of a selected collected fraction of a material, such as a whole blood sample.

As discussed above, the buoy suspension fractionation system 10 can be used in a method of isolating a fraction from a suspension. The separation container 12 can be centrifuged for a period that is appropriate for the suspension. The buoy 30 in the separation container 12 is allowed to reach an equilibrium position within the formed fractions. Typically, the buoy moves from the separation container bottom to an equilibrium position within and/or between the fractions. In some embodiments, the buoy 30 is configured with the transverse dimension cross-sectional area of the buoy near the equilibrium interface to be substantially the buoy's maximum transverse cross-sectional area $A_1$, as illustrated in FIG. 1. As discussed above, the design of the buoy can be determined to position a maximum cross sectional area of the buoy within a selected fraction, such as the red blood cell fraction, of a whole blood sample. The positioning of the buoy can be based upon the density of the buoy which is determined from the density of a selected fraction, such as a red blood cell fraction. Therefore, the buoy can be created or formed to include a density to substantially position it within a red blood cell fraction, for example, of a sample to be separated. For example, the buoy can have a density of about 1.010 g/cc to about 1.1 g/cc. Exemplary densities include about 1.058 g/cc to about 1.070 g/cc, including about 1.064 g/cc. Such a buoy design effects a substantially maximum change in displacement of a volume of fractionated suspension below an equilibrium interface and effects a substantially maximum change in displacement of a volume of fractionated suspension above the equilibrium interface relative to the axial displacement of the buoy resulting in more precisely controlling the selected fraction isolation. As discussed above, the buoy, according to various embodiments, has a maximum cross section at a selected region. Positioning a maximum cross section within a selected fraction or area of a sample will maximum displacement of the sample relative to the buoy do to the maximum cross section of the buoy. In other words, by positioning the biggest portion of the buoy within a selected sample the biggest portion of the sample is displaced because of the displacement of the buoy.

Particulates are concentrated using a guide surface 42, 90, 138, 152, 162 of the buoy that is inclined to an accumulation position near a perimeter of the buoy. The guide surface can be inclined relative to the buoy sidewall substantially throughout a length of the guide surface. The guide surface can be defined by or positioned near the top wall of the buoy.

The particulates are conveyed along the guide surface of the buoy to a collection space. The particulates can be conveyed along a substantially planar path to the collection space. According to various embodiments, however, the guide surface can also include multiple angles 42, 44 and 152, 154 and/or contours 96, 98. The particulates can be selected from the group consisting of platelets, stromal cells, white blood cells, or the like.

Figure 14:
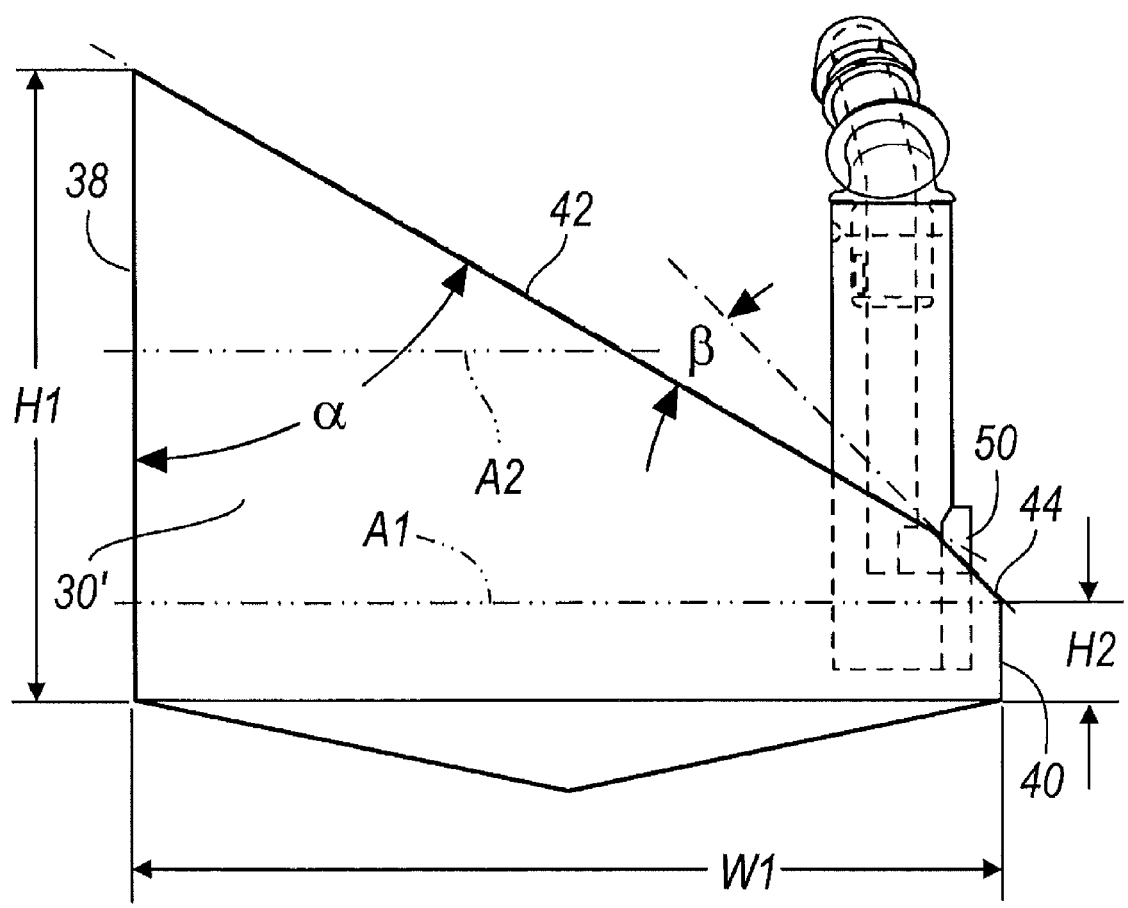
FIG. 14 is a plan view of a buoy, according to various embodiments.
Figure 15:
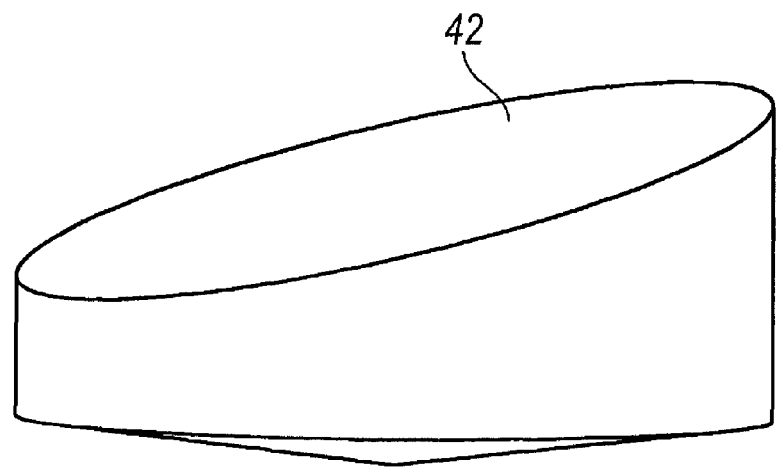
FIG. 15 is a plan view of a buoy, according to various embodiments.
Figure 16:
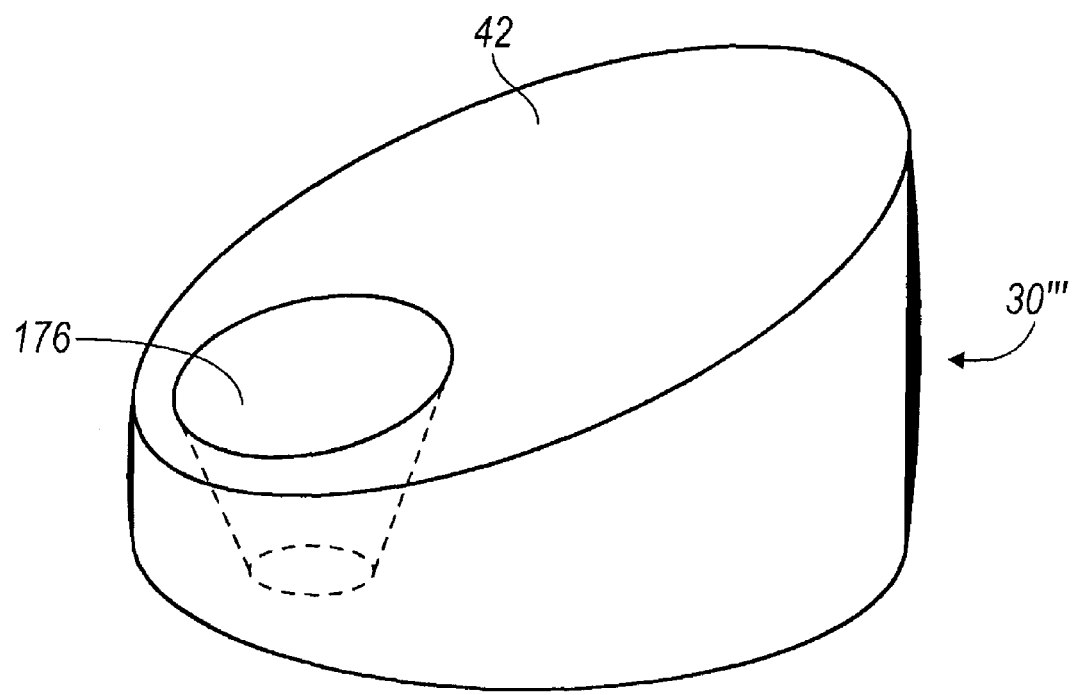
FIG. 16. is a plan view of a buoy, according to various embodiments.

A desired fraction is withdrawn from the collection space through an access port. In some embodiments, the desired fraction can be withdrawn from the collection space by tipping the separation container and pouring the desired fraction out through an access port or out through the container top. This is especially true when only the buoy 30', 30", 30''' is present (FIGS. 14, 15, and 16).

In some embodiments, the method of isolating a fraction can further comprise isolating an isolated fraction in a collection compartment between the guide surface of the buoy 30, 80, 120, 140, 160, 180, 190 and an isolator 32, 82, 122, 142, 162, 182, 192 coupled to the buoy and withdrawing the isolated fraction through a withdraw port through the isolator.

The buoy suspension fractionation system can be used in a method of isolating and re-suspending particulates for withdrawal. The method begins by filling a separation container through an access port with a suspension. The separation container has a buoy with a tuned density and the suspension can contact the buoy.

The separation container can be centrifuged to cause the suspension to separate into fractions of varying densities. Centrifugation can occur for a period that is appropriate for the suspension, such as about five to about thirty minutes.

The buoy in the separation container is allowed to reach equilibrium within the fluid between two or more fractions. Typically the buoy moves from the separation container bottom to equilibrium within the fractions. In some embodiments, particulates can be concentrated using a guide surface of the buoy. The guide surface can be inclined to an accumulation position 44, 92 near a buoy perimeter location. According to various embodiments, the guide surface can be inclined relative to a buoy sidewall substantially throughout the length of the guide surface. The particulates can be conveyed along the guide surface of the buoy to a collection port. The particulates can be platelets, stromal cells, white blood cells, or the like.

A fraction is isolated in a collection compartment between the guide surface of the buoy and an isolator coupled to the buoy. In some embodiments, there can be a fraction 308 located above the isolator that can be withdrawn prior to withdrawing a first increment of the second fraction 310. In other embodiments, the collection vent tube 203 can eliminate the need to withdraw the fraction 308 located above the isolator prior to withdrawing the first increment of the second fraction 310.

Figure 19:
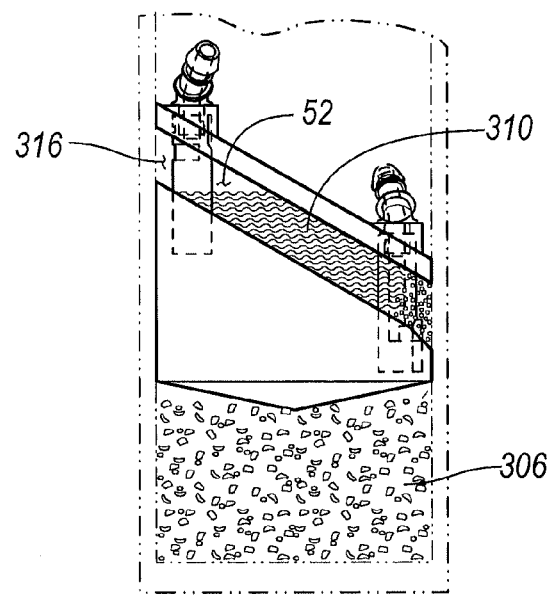
FIG. 19 is an environmental view of a selected component being withdrawn from a separation device according to various embodiments.

Particulates within the isolated fraction can be re-suspended within the collection compartment by moving an agitator 130, 316 (FIGS. 11A and 19) in the separation container 12 to agitate the isolated fraction to create a more uniform particulate distribution within the isolated fraction. In some embodiments, the agitator is an air bubble 316 that is created by withdrawing the first increment of the isolated fraction 310 from a collection compartment allowing air to enter the collection compartment through the collection vent 58. In other embodiments, the agitator 130 is a mechanical agitator placed in the collection compartment.

The re-suspended isolated fraction can be withdrawn from the collection compartment.

Figure 20:
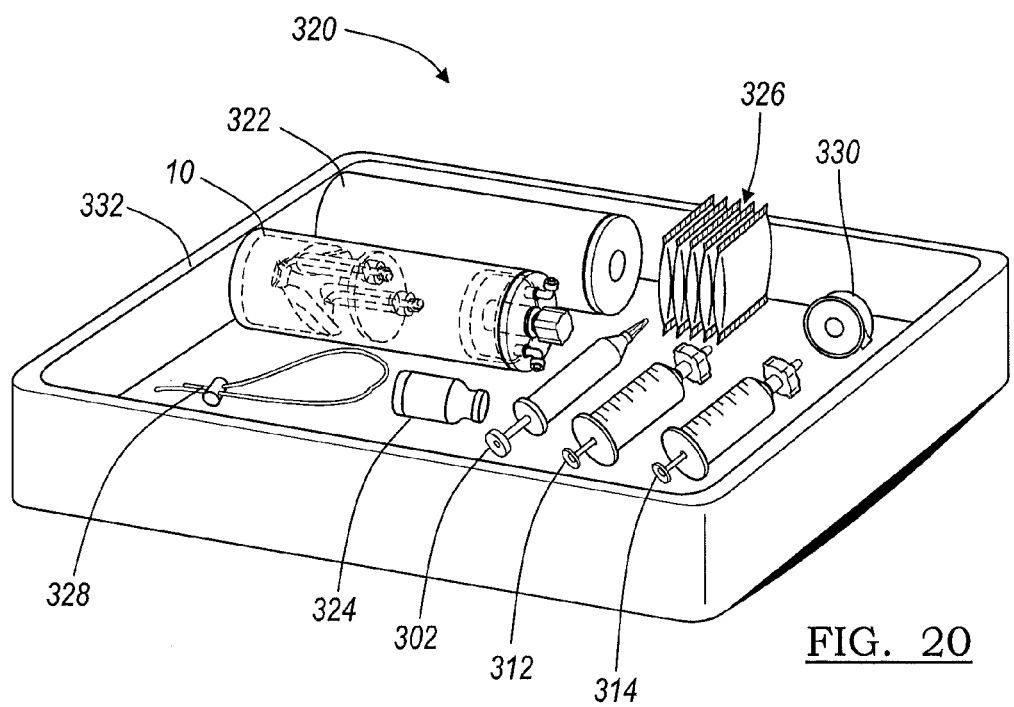
FIG. 20 is a kit according to various embodiments, for separation and extraction of a selected component of a suspension.

For illustration and for efficiency of use of the system, the various components can be included in a kit 320, illustrated in FIG. 20. The kit 320 includes the fractionation system 10 and a counterweight container 322 if required for centrifuge balance. The kit 320 can also include various syringes 302, 312, and 314 for extraction and application of the fractions and samples. The kit 320 can also include bandages 3226, tape 330, a tourniquet 328, and various additive materials. The kit 320 can include a container 332 for transport and sterilization.

Thus, embodiments of a buoy suspension fractionation system are disclosed. One skilled in the art will appreciate that the teachings can be practiced with embodiments other than those disclosed. The disclosed embodiments are presented for purposes of illustration and not limitation, and the invention is only limited by the claims that follow.

The invention claimed is:

1. A buoy suspension fractionation system, comprising:
   a separation container and an access port through at least a portion of the separation container, the separation container is enclosed by a container wall, a container bottom, and a container top; and,
   a buoy in the separation container, the buoy having a tuned density and configured to reach an equilibrium position in a suspension material, the buoy comprising a buoy upper surface and a buoy sidewall defining a height, a transverse dimension through a center portion of the buoy, and a perimeter, the buoy further comprising;
      a guide surface on the buoy upper surface, the guide surface having a collection space above the buoy upper surface and the guide surface being inclined to an accumulation position near the buoy perimeter; and
   a collection port extending from the guide surface nearer the buoy perimeter than the center portion of the buoy and communicating with the access port and communicating with the collection space above the buoy upper surface.

2. The buoy suspension fractionation system as in claim 1 wherein the buoy includes a maximum transverse dimension configured to be positioned near an equilibrium interface between two separated fractions of the suspension and substantially defining a buoy maximum cross-sectional area.

3. The buoy suspension fractionation system as in claim 2 wherein movement of the buoy near an equilibrium interface results in substantially maximum change in displacement of a fractionated suspension below the equilibrium interface and substantially maximum change in displacement of a fractionated suspension above the equilibrium interface relative to change in axial orientation of the buoy relative to the interface.

4. The buoy suspension fractionation system as in claim 1 wherein the guide surface is inclined relative to the buoy sidewall for a distance of more than about two-thirds the buoy transverse dimension.

5. The buoy suspension fractionation system as in claim 4 wherein the guide surface is inclined relative to the buoy sidewall substantially throughout an entire distance of the guide surface.

6. The buoy suspension fractionation system as in claim 1 wherein the guide surface is inclined in relation to the buoy sidewall at an average angle of about 10 degrees to about 70 degrees.

7. The buoy suspension fractionation system as in claim 1 wherein the guide surface is substantially planar for the entire transverse dimension of the buoy.

8. The buoy suspension fractionation system as in claim 1 wherein the guide surface is inclined substantially outwardly toward the buoy perimeter.

9. The buoy suspension fractionation system as in claim 8, wherein the guide surface extends from a first edge of the buoy perimeter along the transverse dimension and substantially through a center of the buoy to a second edge of the buoy perimeter different from the first edge.

10. The buoy suspension fractionation system as in claim 1 further comprising,
    an isolator coupled to the buoy, the isolator comprising a spacer to position the isolator apart from the buoy to create a collection area within the collection space.

11. The buoy suspension fractionation system as in claim 10 further comprising,
    a withdraw port carried on the isolator communicating with the access port and the collection area.

12. The buoy suspension fractionation system as in claim 10 wherein the isolator has an isolator volume and the buoy has a buoy volume; wherein a first combination of both of the isolator volume and the buoy volume below an equilibrium interface is operable to be greater than a second combination of both of the isolator volume and the buoy volume above the equilibrium interface.

13. The buoy suspension fractionation system as in claim 10 wherein the isolator is configured to move from an open position apart from the buoy to a closed position near the buoy.

14. The buoy suspension fractionation system as in claim 10 wherein the isolator has an isolator volume and the buoy has a buoy volume; wherein the isolator volume is substantially less than the buoy volume.

15. The buoy suspension fractionation system as in claim 10 wherein the isolator has collection openings.

16. The buoy suspension fractionation system as in claim 10 further comprising,
    a collection vent passage through the isolator to equalize pressure when fluid is withdrawn from the collection area.

17. The buoy suspension fractionation system as in claim 16 further comprising,
    a collection valve communicating with the collection vent.

18. The buoy suspension fractionation system as in claim 16 further comprising,
    a collection vent tube communicating with the collection vent and air above where a suspension would be located in a separation container.

19. The buoy suspension fractionation system as in claim 10 further comprising,
    a mechanical agitator carried in the collection area.

20. The buoy suspension fractionation system as in claim 1 wherein the collection port is formed in a member that extends from the guide surface and is located near the buoy perimeter and is in direct fluid communication with the collection space at the buoy perimeter.

21. The buoy suspension fractionation system as in claim 20 further comprising,
a precision collection region interposed between the guide surface and the buoy perimeter, wherein the precision collection region includes an incline greater than the guide surface that extends towards the buoy perimeter; wherein the collection port is in direct fluid communication with the precision collection region.

22. The buoy suspension fractionation system as in claim 1 wherein when the separation container is at rest, the buoy perimeter and the container wall form an interference fit operable to hold the buoy at a position in the separation container and when the separation container is centrifuged a clearance is defined between the buoy perimeter and the container wall allowing the buoy to move within the separation container and at least a portion of the suspension material to pass between the buoy perimeter and the container wall.

23. The buoy suspension fractionation system as in claim 1 wherein the separation container is a separation tube.

24. A buoy for a suspension fractionation system, comprising:
a buoy having a tuned density and configured to reach an equilibrium point in a suspension, the buoy comprising a buoy upper surface, a buoy sidewall defining a height, a buoy transverse dimension, and a buoy perimeter, the buoy further comprising;
a collection port communicating with a collection space above the buoy upper surface;
a guide surface on the buoy upper surface, the guide surface being substantially planar and inclined from a first point at an edge of the buoy for a distance of more than two thirds the buoy transverse dimension towards a second point at the edge of the buoy;
an isolator coupled to the buoy, the isolator comprising a spacer to position the isolator apart from the buoy to create a collection compartment in the collection space between the isolator and the buoy upper surface; and
a withdraw port carried on the isolator communicating with the collection port.

25. The buoy suspension fractionation system as in claim 24 wherein the buoy transverse dimension includes a cross-sectional area of the buoy configured near an equilibrium interface to be substantially a maximum cross-sectional area of the buoy.

26. The buoy suspension fractionation system as in claim 25 wherein movement of the buoy near an equilibrium interface is operable to result in substantially maximum change in displacement of a fraction below the equilibrium interface and substantially maximum change in displacement of a fraction above the equilibrium interface relative to an axis of buoy relative to the equilibrium interface.

27. The buoy system as in claim 24 further comprising,
a collection vent on the isolator operable to equalize pressure when fluid is withdrawn from the collection space.

28. The buoy system as in claim 24 further comprising,
a collection valve communicating with the collection port.

29. The buoy system as in claim 28 further comprising,
a collection vent tube communicating with the collection vent above where a suspension would be located in a separation container.

30. The buoy system as in claim 24 wherein the collection port is located near the buoy perimeter and is in direct fluid communication with a volume at the second edge.

31. The buoy system as in claim 24 wherein the isolator has collection openings.

32. The buoy system as in claim 30 further comprising,
a precision collection region interposed between the guide surface and the buoy perimeter at the second edge, wherein the precision collection region includes an angle of incline towards the second edge that is greater than a majority of an angle of the incline of the guide surface.

33. The buoy system as in claim 24 wherein an isolator volume is substantially less than a buoy volume.

34. The buoy system as in claim 24 wherein a first isolator volume and a first buoy volume combined below an equilibrium interface is operable to be greater than a second isolator volume and a second buoy volume combined above the equilibrium interface.

35. A buoy suspension fractionation system, comprising:
a separation container and an access port through at least a portion of the separation container, the separation container is enclosed by a container wall, a container bottom, and a container top; and,
a buoy in the separation container, the buoy having a tuned density and configured to reach an equilibrium position in a suspension, the buoy comprising a buoy upper surface and a buoy sidewall defining a height, a transverse dimension, and a perimeter, the buoy further comprising;
a guide surface on the buoy upper surface, the guide surface having a collection space above the buoy upper surface and the guide surface being inclined to an accumulation position near the buoy perimeter;
an isolator coupled to the buoy, the isolator comprising a spacer to position the isolator apart from the buoy to create a collection area in a space between the buoy and the isolator;
a collection vent passage through the isolator to equalize pressure when fluid is withdrawn from the collection area; and
a collection valve communicating with the collection vent.

36. The buoy suspension fractionation system as in claim 35 wherein the guide surface is inclined from one point on the buoy sidewall to a second point on the buoy sidewall though a center portion of the buoy for a distance of more than about two-thirds the buoy transverse dimension.

37. The buoy suspension fractionation system as in claim 35 wherein the guide surface is inclined relative to the buoy sidewall in one direction substantially throughout a length of the guide surface.

38. The buoy suspension fractionation system as in claim 35 wherein the guide surface is substantially planar.

39. The buoy suspension fractionation system as in claim 35, wherein the guide surface extends from a first edge of the buoy perimeter along the transverse dimension and substantially through a center of the buoy to a second edge of the buoy perimeter;
wherein the guide surface defines at least two thirds a width of the buoy.

40. The buoy suspension fractionation system as in claim 35, further comprising a collection port communicating with the access port and communicating with the collection space above the buoy upper surface.

41. The buoy suspension fractionation system as in claim 35 further comprising,
a withdraw port carried on the isolator communicating with the access port and the collection area.

42. The buoy suspension fractionation system as in claim 35 wherein the isolator has an isolator volume and the buoy has a buoy volume; wherein the isolator volume is substantially less than the buoy volume.

43. The buoy suspension fractionation system as in claim 40 wherein the collection port is in communication with a volume at the buoy perimeter.

44. The buoy suspension fractionation system as in claim 43 further comprising,
   a precision collection region interposed between the guide surface and the buoy perimeter in the volume at the buoy perimeter.

45. A buoy suspension fractionation system, comprising:
   a separation container and an access port through at least a portion of the separation container, the separation container is enclosed by a container wall, a container bottom, and a container top; and,
   a buoy in the separation container, the buoy having a tuned density and configured to reach an equilibrium position in a suspension, the buoy comprising a buoy upper surface and a buoy sidewall defining a height, a transverse dimension, and a perimeter, the buoy further comprising;
      a guide surface on the buoy upper surface, the guide surface having a collection space above the buoy upper surface and the guide surface being inclined to an accumulation position near the buoy perimeter;
   an isolator coupled to the buoy, the isolator comprising a spacer to position the isolator apart from the buoy to create a collection area in a space between the buoy and the isolator;
   a collection vent passage through the isolator to equalize pressure when fluid is withdrawn from the collection area; and
   a collection vent tube communicating with the collection vent and air above where a suspension would be located in a separation container.

46. The buoy suspension fractionation system as in claim 45 wherein the buoy includes a maximum transverse dimension configured to be positioned near an equilibrium interface between two separated fractions of the suspension and substantially defining a buoy maximum cross-sectional area.

47. The buoy suspension fractionation system as in claim 45 wherein the guide surface is inclined relative to the buoy sidewall in one direction substantially throughout a length of the guide surface.

48. The buoy suspension fractionation system as in claim 45 wherein the guide surface is substantially planar.

49. The buoy suspension fractionation system as in claim 45, wherein the guide surface extends from a first edge of the buoy perimeter along the transverse dimension and substantially through a center of the buoy to a second edge of the buoy perimeter;
   wherein the guide surface defines at least two thirds a width of the buoy.

50. The buoy suspension fractionation system as in claim 45, further comprising a collection port communicating with the access port and communicating with the collection space above the buoy upper surface.

51. The buoy suspension fractionation system as in claim 45 further comprising,
   a withdraw port carried on the isolator communicating with the access port and the collection area.

52. The buoy suspension fractionation system as in claim 45 further comprising,
   a precision collection region interposed between the guide surface and the buoy perimeter in the volume at the buoy perimeter.

53. The buoy suspension fractionation system as in claim 24, wherein the buoy transverse dimension passes through a center of the buoy.

* * * * *